US007803913B2

(12) United States Patent
Dimitrov et al.

(10) Patent No.: US 7,803,913 B2
(45) Date of Patent: Sep. 28, 2010

(54) IDENTIFICATION OF NOVEL BROADLY CROSS-REACTIVE NEUTRALIZING HUMAN MONOCLONAL ANTIBODIES USING SEQUENTIAL ANTIGEN PANNING OF PHAGE DISPLAY LIBRARIES

(75) Inventors: Dimiter S Dimitrov, Rockville, MD (US); Mei-Yun Zhang, Frederick, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 435 days.

(21) Appl. No.: 10/513,725

(22) PCT Filed: May 6, 2003

(86) PCT No.: PCT/US03/14292

§ 371 (c)(1),
(2), (4) Date: Jan. 25, 2005

(87) PCT Pub. No.: WO03/092630

PCT Pub. Date: Nov. 13, 2003

(65) Prior Publication Data

US 2005/0123900 A1     Jun. 9, 2005

Related U.S. Application Data

(60) Provisional application No. 60/378,408, filed on May 6, 2002.

(51) Int. Cl.
 C07K 16/00 (2006.01)
 A61K 39/42 (2006.01)
(52) U.S. Cl. ............... 530/387.1; 530/389.4; 424/160.1
(58) Field of Classification Search ............. 530/387.1, 530/389.4; 424/160.1
See application file for complete search history.

(56) References Cited

U.S. PATENT DOCUMENTS

| | | | |
|---|---|---|---|
| 5,518,723 A | 5/1996 | DeVico et al. | |
| 5,571,681 A * | 11/1996 | Janda ........................... | 506/10 |
| 5,804,440 A | 9/1998 | Burton et al. | |
| 5,925,741 A | 7/1999 | Gershoni | |
| 6,030,772 A | 2/2000 | Devico et al. | |
| 6,135,941 A * | 10/2000 | Hillman et al. ............ | 536/23.1 |
| 6,261,558 B1 * | 7/2001 | Barbas et al. ............ | 424/133.1 |
| 6,680,209 B1 * | 1/2004 | Buechler et al. ............ | 436/518 |
| 7,084,257 B2 * | 8/2006 | Deshpande et al. ...... | 530/387.9 |
| 2003/0018004 A1 | 1/2003 | Kingsman et al. | |
| 2003/0133939 A1 | 7/2003 | Ledbetter et al. | |
| 2003/0147881 A1 | 8/2003 | Cheung et al. | |
| 2004/0039172 A1 | 2/2004 | Haynes et al. | |

FOREIGN PATENT DOCUMENTS

| | | |
|---|---|---|
| EP | 1 054 018 A1 | 11/2000 |
| WO | WO 91/00360 A1 | 1/1991 |
| WO | WO 93/15747 A1 | 8/1993 |
| WO | WO 94/07922 A1 | 4/1994 |
| WO | WO 96/15273 A1 | 5/1996 |
| WO | WO 99/24464 A1 | 5/1999 |
| WO | WO 00/40616 A1 | 7/2000 |
| WO | WO 00/55207 A1 | 9/2000 |
| WO | WO 00/69914 A2 | 11/2000 |
| WO | WO 02/093519 A2 | 11/2002 |
| WO | WO 03/033666 A2 | 4/2003 |
| WO | WO 03/092630 A2 | 11/2003 |
| WO | WO 03/095492 A1 | 11/2003 |

OTHER PUBLICATIONS

Binley et al., Human Antibody Responses to HIV Type 1 Glycoprotein 41 Cloned in Phage Display Libraries Suggest Three Major Epitopes are Recognized and Give Evidence for Conserved Antibody Motifs in Antigen Binding, AIDS Research and Human Retroviruses, 12(10): 911-924.*
Burton et al., *Science*, 266,1024-1027 (1994).
Celada et al., *J. Exp. Med.*, 172, 1143-1150 (1990).
Chan et al., *Cell*, 93, 681-684 (1998).
Conley et al., *PNAS*, 91, 3348-3352 (1994).
Devico et al., *Virology*, 218, 258-263 (1996).
Dimitrov, *Cell*, 101, 697-702 (2000).
Dimitrov, *Nat. Med.*, 2(6), 640-641 (1996).
Gershoni et al., *FASEB J.*, 7,1185-1187 (1993).
Jellis et al., *Gene*, 137, 63-68 (1993).
Kang et al., *J. Virol.*, 68(9), 5854-5862 (1994).
Lacasse et al., *Science*, 283, 357-362 (1999).
Li et al., *J. Peptide Res.*, 57, 507-518 (2001).
Moulard et al., *PNAS*, 99 (10), 6913-6918 (2002).
Muster et al., *J. Virol.*, 67 (11), 6642-6647 (1993).
Sodroski, *Cell*, 99, 243-246 (1999).
Sullivan et al., *J. Virol.*, 72(6), 4694-4703 (1998).
Trkola et al., *J. Virol.*, 70 (2), 1100-1108 (1996).
Zwick et al., *J. Virol.*, 75 (22),10892-10905 (2001).
Hoogenboom et al., *Immunotechnology*, 4, 1-20 (1998).

(Continued)

*Primary Examiner*—Amber D. Steele
(74) *Attorney, Agent, or Firm*—Leydig, Voit & Mayer, Ltd.

(57) ABSTRACT

The present invention provides a method of identifying novel broadly crossreactive neutralizing monoclonal antibodies using sequential antigen panning of phage display libraries, antibodies obtained in accordance with such a method, as well as fusion proteins and conjugates comprising same, and related isolated or purified nucleic acid molecules, vectors, host cells, compositions, and methods of use to inhibit an infection, reduce the severity of an infection, treat an infection, and inhibit cancer.

20 Claims, 4 Drawing Sheets

OTHER PUBLICATIONS

Ahlborg et al., "Immune responses in congenic mice to multiple antigen peptides based on defined epitopes from the malaria antigen Pf332," *Immunology*, 88 (4), 630-635 (1996).

Barbas et al., "In vitro evolution of a neutralizing human antibody to human immunodeficiency virus type 1 to enhance affinity and broaden strain cross-reactivity," *Proc. Natl. Acad. Sci. USA*, 91 (9), 3809-3813 (1994).

Binley et al., "Human Antibody Responses to HIV Type 1 glycoprotein 41 Cloned in Phage Display Libraries Suggest Three Major Epitopes Are Recognized and Give Evidence for Conserved Antibody Motifs in Antigen Binding," *AIDS Research and Human Retroviruses*, 12 (10), 911-924 (1996).

Boots et al., "Anti-human immunodeficiency virus type 1 human monoclonal antibodies that bind discontinuous epitopes in the viral glycoproteins can identify mimotopes from recombinant phage peptide display libraries," *AIDS Res. Hum. Retrovir.*, 13 (18), 1549-1559 (1997).

Brenneman et al., "VIP and d-ala-peptide T-amide release chemokines which prevent HIV-1 GP120-induced neuronal death," *Brain Res.*, 838, 27-36 (1999).

Broliden et al., "Functional HIV-1 specific IgA antibodies in HIV-1 exposed, persistently IgG seronegative female sex workers," *Immunol. Lett.*, 79 (1-2), 29-36 (2001).

Burioni et al., "Recombinant human Fab to glycoprotein D neutralizes infectivity and prevents cell-to-cell transmission of herpes simplex viruses 1 and 2 in vitro," *Proc. Natl. Acad. Sci. USA*, 91 (4), 355-359 (1994).

Cheng et al., "Construction, Expression and Characterization of the Engineered Antibody Against Tumor Surface Antigen," *Cell Research*, 13 (1), 35-48 (2003).

Choudhry et al., "Cross-reactive HIV-1 neutralizing monoclonal antibodies selected by screening of an immune human phage library against an envelope glycoprotein (gp140) isolated from a patient (R2) with broadly HIV-1 neutralizing antibodies," *Virology*, 363 (1), 79-90 (2007).

Chow et al., "Conserved Structures Exposed in HIV-1 Envelope Glycoproteins Stabilized by Flexible Linkers as Potent Entry Inhibitors and potential Immunogens," *Biochem.*, 41, 7176-7182 (2002).

Dalgleish et al., "The CD4 (T4) Antigen is an Essential Component of the Receptor for the AIDS Retrovirus," *Nature*, 312 (5996), 763-767 (1984).

Deen et al., "A soluble form of CD4 (T4) protein inhibits AIDS virus infection," *Nature*, 331 (6151), 82-84 (1988).

Dey et al., "Neutralization of human immunodeficiency virus type 1 by sCD4-17b, a single-chain chimeric protein, based on sequential interaction of gp120 with CD4 and coreceptor," *J. Virol.*, 77 (5), 2859-2865 (2003).

Dimitrov, "Virus Entry: Molecular Mechanisms and Biomedical Applications," *Nature Reviews Microbiology*, 2, 109-122 (2004).

Finnegan et al., "Antigenic properties of the human immunodeficiency virus transmembrane glycoprotein during cell-cell fusion," *J. Virol.*, 76(23), 12123-12134 (2002).

Fisher et al., "HIV infection is blocked in vitro by recombinant soluble CD4," *Nature*, 331 (6151), 76-78 (1988).

Golding et al., "Increased association of glycoprotein 120-CD4 with HIV type 1 coreceptors in the presence of complex-enhanced anti-CD4 monoclonal antibodies," *AIDS Res Hum Retroviruses*, 15 (2), 149-159 (1999).

Gorny et al., "The v3 loop is accessible on the surface of most human immunodeficiency virus type 1 primary isolates and serves as a neutralization epitope," *J. Virol.*, 78 (5), 2394-2404 (2004).

Goudsmit et al., ",Human immunodeficiency virus type 1 neutralization epitope with conserved architecture elicits early type-specific antibodies in experimentally infected chimpanzees," *Proc. Natl. Acad. Sci. USA*, 85 (12), 4478-4482 (1988).

Javaherian et al., "Principal neutralizing domain of the human immunodeficiency virus type 1 envelope protein," *Proc. Natl. Acad. Sci. USA*, 86 (17), 6768-6772 (1989).

Kilby et al., "Potent suppression of HIV-1 replication in humans by T-20, a peptide inhibitor of gp41-mediated virus entry," *Nat. Med.*, 4 (11), 1302-1307 (1998).

Klatzmann et al., "T-lymphocyte T4 Molecule Behaves as the Receptor for Human Retrovirus LAV," *Nature*, 312 (5996), 767-768 (1984).

Kwong et al., "Structure of an HIV gp120 envelope glycoprotein in complex with the CD4 receptor and a neutralizing human antibody," *Nature*, 393 (6686), 648-659 (1998).

Labrijn et al. "Access of Antibody Molecules to the Conserved Coreceptor Binding Site on Glycoprotein gp120 Is Sterically Restricted on Primary Human Immunodeficiency Virus Type 1," *J. Virol.*, 77 (19), 10557-10565 (2003).

Lapham et al., "Evidence for cell-surface association between fusin and the CD4-gp120 complex in human cell lines," *Science*, 274 (5287), 602-605 (1996).

Liao et al., "Immunogenicity of constrained monoclonal antibody A32-human immunodeficiency virus (HIV) Env gp120 complexes compared to that of recombinant HIV type 1 gp120 envelope glycoproteins," *J. Virol.*, 78 (10), 5270-5278 (2004).

Lomholt et al., "Neisseria gonorrhoeae IgA1 proteases share epitopes recognized by neutralizing antibodies," *Vaccine*, 13 (13), 1213-1219 (1995).

Mirzabekov et al., "Paramagnetic proteoliposomes containing a pure, native, and oriented seven-transmembrane segment protein, CCR5," *Nat. Biotech.*, 18 (6), 649-654 (2000).

Mirzabekov et al., "Enhanced expression, native purification, and characterization of CCR5, a principal HIV-1 coreceptor," *J Biological Chemistry*, 274 (40), 28745-28750 (1999).

Moore et al., "Antibody cross-competition analysis of the human immunodeficiency virus type 1 gp120 exterior envelope glycoprotein," *J. Virol.*, 70 (3), 1863-1872 (1996).

Moore et al., "Probing the Structure of the V2 Domain of Human Immunodeficiency Virus Type 1 Surface Glycoprotein gp120 with a Panel of Eight Monoclonal Antibodies: Human Immune Response to the V1 and V2 Domains," *Journal of Virology*, 67 (10), 6136-6151 (1993).

Myers et al., "Targeting Immune Effector Molecules to Human Tumor Cells Through Genetic Delivery of 5T4-specific scFv Fusion Proteins," *Cancer Gene Therapy*, 9 (11), 884-896 (2002).

Palker et al., "Type-specific neutralization of the human immunodeficiency virus with antibodies to env-encoded synthetic peptides," *Proc. Natl. Acad. Sci. USA*, 85 (6), 1932-1933 (1988).

Parren et al., "Protection against HIV-1 infection in hu-PBL-SCID mice by passive immunization with a neutralizing human monoclonal antibody against the gp120 CD4-binding site," *AIDS*, 9 (6), F1-F6 (1995).

Parren et al., "Neutralization of Human Immonudeficiency Virus Type 1 by Antibody to gp120 is Determined Primarily by Occupancy of Sites on the Virion Irrespective of Epitope Specificity," *Journal of Virology*, 72 (5), 3512-3519 (1998).

Parren et al., "The Antiviral Activity of Antibodies in Vitro and in Vivo," *Advances in Immunology*, 77, 195-262 (2001).

Prabakaran et al., "Structural Mimicry of CD4 by a Cross-reactive HIV-1 Neutralizing Antibody with CDR-H2 and H3 Containing Unique Motifs," *J. Mol. Biol.*, 357, 82-89 (2006).

Ray et al., "Selection of Single Chain Variable Fragments (scFv) Against the Glycoprotein Antigen of the Rabies Virus from a Human Synthetic scFv Phage Display Library and their Fusion with the Fc Region of Human IgG1," *Clin. Exp. Immunol.* 125 (1), 94-101 (2001).

Rizzuto et al., "A Conserved HIV gp120 Glycoprotein Structure Involved in Chemokine Receptor Binding," *Science*, 280 (5371), 1949-1953 (1998).

Rizzuto et al., "Fine Definition of a Conserved CCR5-Binding Region on the Human Immunodeficiency Virus Type 1 Glycoprotein 120," *AIDS Res. Hum. Retrovir.*, 16 (8), 741-749 (2000).

Sattentau et al., "Conformational Changes Induced in the Envelope Glycoproteins of the Human and Simian Immunodeficiency Viruses by Soluble Receptor Binding," *J. Virol.*,67 (12), 7383-7393 (1993).

Sattentau et al., "Conformational Changes Induced in the Human Immunodeficiency Virus Envelope Glycoprotein by Soluble CD4 Binding," *J. Exp. Med.*, 174 (2), 407-415 (1991).

Thali et al., "Characterization of Conserved Human Immunodeficiency Virus Type 1 gp120 Neutralization Epitopes Exposed upon gp120-CD4 Binding," *Journal of Virology*, 67 (7), 3978-3988 (1993).

Trkola et al., "CD-4 Dependent, Antibody-Sensitive Interactions Between HIV-1 and its Co-Receptor CCR-5," *Nature*, 384 (6605), 184-187 (1996).

Ugolini et al., "Inhibition of Virus Attachment to CD4+Target Cells is a Major Mechanism of T Cell Line-adapted HIV-1 Neutralization," *J. Exp. Med.*, 186 (8), 1287-1298 (1997)).

Vogel et al., "Cross reactive anti-tetanus and anti-melittin Fab fragments by phage display after tetanus toxoid immunisation," *Hum Antibodies Hybridomas*, 7 (1), 11-20 (1996).

Wu et al., "CD4-Induced Interaction of Primary HIV-1 gp120 Gycoproteins with the Chemokine Receptor CCR-5," *Nature*, 384 (6605), 179-183 (1996).

Wyatt et al. "The Antigenic Structure of the HIV gp120 Envelope Glycoprotein," *Nature*, 393 (6686), 705-711 (1998).

Wyatt et al., "Involvement of the V1/V2 Variable Loop Structure in the Exposure of Human Immunodeficiency Virus Type 1 gp120 Epitopes Induced by Receptor Binding," *Journal of Virology*, 69 (9), 5723-5733 (1995).

Wyatt et al., "The HIV-1 Envelope Glycoproteins: Fusogens, Antigens, and Immunogens," *Science*, 280 (5371), 1884-1888 (1998).

Xiang et al., "Characterization of CD4-induced epitopes on the HIV type 1 gp120 envelope glycoprotein recognized by neutralizing human monoclonal antibodies," *AIDS Res Hum Retroviruses*, 18 (16), 1207-1217 (2002).

Xiao et al., "Constitutive cell surface association between CD4 and CCR5," *Proc. Natl. Acad. Sci., USA* 96 (13), 7496-7501 (1999).

Zhang et al., "Broadly cross-reactive HIV neutralizing human monoclonal antibody Fab selected by sequential antigen panning of a phage display library," *J. Immunol. Met.*, 283 (1-2), 17-25 (2003).

Zhang et al., "Identification and characterization of a new cross-reactive human immunodeficiency virus type 1-neutralizing human monoclonal antibody," *J. Virol.*, 78 (17), 9233-9242 (2004).

Zhang et al., "Improved breadth and potency of an HIV-1-neutralizing human single-chain antibody by random mutagenesis and sequential antigen panning," *J. Mol. Biol.*, 335 (1), 209-219 (2004).

Zhang et al., "Novel approaches for identification of broadly cross-reactive HIV-1 neutralizing human monoclonal antibodies and improvement of their potency," *Curr. Pharm. Des.*, 13 (2), 203-212 (2007).

Zhang et al., "Pharmacokinetics of Plasma Enfuvirtide After Subcutaneous Administration to Patients with Human Immunodefiency Virus: Inverse Gaussian Density Absorption and 2-compartment Disposition," *Clin. Pharmacol. Ther.*, 72 (1), 10-19 (2002).

Wu et al., "Multimerization of a Chimeric Anti-CD20 Single-Chain Fv-Fc Fusion Protein is Mediated Through Variable Domain Exchange," *Protein Engineering*, 14 (12), 1025-1033 (2001).

Yang et al., *Journal of Virology*, 74(12), 5716-5725 (Jun. 2000).

\* cited by examiner

Flow chart of sequential antigen panning (m12 and m14)

pComb3H phage
 ↓ Preabsorption on pre-washed M-280 streptavidin beads
 ↓ Depletion with sCD4
 ↓ 1<sup>st</sup> round of panning (rp) against 50 nM biotinylated gp140$_{89.6}$-sCD4

1<sup>st</sup> round panned library
 ↓ Preabsorption on pre-washed M-280 streptavidin beads
 ↓ Depletion with sCD4
 ↓ 2<sup>nd</sup> rp against 10 nM biotinylated gp140$_{89.6}$-sCD4 complexes 2<sup>nd</sup> round panned library
 ↓ Preabsorption on pre-washed M-280 streptavidin beads
 ↓ 3<sup>rd</sup> rp against 2 nM biotinylated gp140$_{89.6}$-sCD4 complexes 3<sup>rd</sup> round panned library
 ↓ 4<sup>th</sup> rp against 2 nM biotinylated gp140$_{HXB2}$-sCD4 complexes 4<sup>th</sup> round panned library
 ↓ screen individual clones from 4<sup>th</sup>, 5<sup>th</sup> and 6<sup>th</sup> round panned libraries by phage ELISA using gp120/140$_{89.6/HBX2}$ and gp120 $_{JRFL}$ and their complexes with sCD4 as antigens selection of clones with highest binding activity to all antigens

FIGURE 1

Flow chart of sequential antigen panning (protocol for m16 and m18)

pComb3H phage library

↓ Preabsorption on pre-washed M-280 streptavidin beads

↓ Depletion with sCD4

↓ 1$^{st}$ round of panning (rp) against 50 nM biotinylated gp140$_{89.6}$-sCD4

1$^{st}$ round panned library

↓ Preabsorption on pre-washed M-280 streptavidin beads

↓ Depletion with sCD4

↓ 2$^{nd}$ rp against 50 nM biotinylated gp140$_{HBX2}$-sCD4 complexes

2$^{nd}$ round panned library

↓ Preabsorption on pre-washed M-280 streptavidin beads

↓ 3$^{rd}$ rp against 10 nM biotinylated gp140$_{89.6}$ envelope glycoprotein

3$^{rd}$ round panned library

↓ Preabsorption on pre-washed M-280 streptavidin beads

↓ 4$^{th}$ rp against 10 nM biotinylated gp140$_{HXB2}$ envelope glycoprotein

4$^{th}$ round panned library

↓ 5$^{th}$ rp against 2 nM biotinylated gp140$_{89.6}$ envelope glycoprotein

5$^{th}$ round panned library

↓ 6$^{th}$ rp against 2 nM biotinylated gp140$_{HXB2}$ envelope glycoprotein

6$^{th}$ round panned library

↓ screen individual clones from 4$^{th}$, 5$^{th}$ and 6$^{th}$ round panned libraries by phage ELISA using gp120/140$_{89.6/HBX2}$ and gp120 $_{JRFL}$ and their complexes with sCD4 as antigens selection of clones with highest binding activity to all antigens

FIGURE 2

```
1                                                           50
    M14-Fd-aa  VQLLESGPGL VKPSQTLSLT CTVSGGSIST GDYYWSWIRQ SPGKGLEWIG
    M18-Fd-aa  VQLLESGPGV VKPSETLSLT CTVSGASVN. .NYYWTWVRQ PPGKGLEWIG
    M12-Fd-aa  VQLLESGPGL VKPSQSLSLT CAISGDSLSS DSTAWNWIRQ SPSRGLEWLG
    M16-Fd-aa  VQLLESGAEV KRPGSSVRVS CQVSGGSFS. .NYAVSWVRQ TPGHGLEWMG
               |                     |          |
                        FR1                      CDR-H1       FR2

51                                          100
    M14-Fd-aa  YISSSGNTYY N..PSLTSRV VISFDTSMNQ FSLKVDSVTA ADTAVYYC..
    M18-Fd-aa  NVYDSGDTNY N..PSLSSRL SLSMDTSKNQ FSLRLSSVTA ADTATYYC..
    M12-Fd-aa  RTYYRSTWFY DYAESVKSRI NINPDTSKSQ FSLQLRSVTP EDTAVYYC..
    M16-Fd-aa  GIIPMFNA.P NYAQKFHGRV TFIADESTRT VHMELRSLRS EDTAVYFCAT
               |                    |
                    CDR-H2                   FR3

101                                         150
    M14-Fd-aa  ARERRVLLWL GFPRGGL..D YWGQGTLVTV .SSASTKGPS VFPLAPSSKS
    M18-Fd-aa  ARYHR..... HFIRGPLSFD YWGRGTLVTV .SSASTKGPS VFPLAPSYKS
    M12-Fd-aa  ARDFNKGAGY NW......FD PWGPGTVVTV .SSASTKGPS VFPLAPSSKS
    M16-Fd-aa  ASEATENDYY QSPTHYYAMD VWGQGTAVTV FSSASTKGPL VFPLAPSSKS
               |                    |          |
                    CDR-H3                FR4              CH1

151                                         200
    M14-Fd-aa  TSGGTASLDC LVKDYFPEPV MVSWNSGALT SGVHTLAAVI QSSGLYSLSS
    M18-Fd-aa  TSGGTSSLDS LVKDSFPEPV MVSWNSGALT RGVHTFPAVI QSAGLYSLIS
    M12-Fd-aa  TSGGTAALDC LVKDYFPEPV MVSWNSGALT SGVHTLAAVL QSSGLYSLSS
    M16-Fd-aa  AFGGTASLDS LVKDSLPEPV MVSWNSGALT TGVRTLAAVI QSAGLYSLIS 201               240
    M14-Fd-aa  VVTVPSSSLG TQTYICNVNR KPSNTKVDNK VEPKSCDKTS
    M18-Fd-aa  VVTVPSSSMG TQTYICNVNR KPSNTKVVNK DEPKSCDKTS
    M12-Fd-aa  VVTVPSSSLG TQTYICNVNR KPSNTKVVKK DEPKSCDKTS
    M16-Fd-aa  VVTVPSSSLG TQTYICNVNR KPSNIKVVNR DEPKSCVKNS
                                                        |
``` m14-Fd-aa is SEQ ID NO: 1
m18-Fd-aa is SEQ ID NO: 2
m12-Fd-aa is SEQ ID NO: 3
m16-Fd-aa is SEQ ID NO: 4

FIGURE 3

```
     1                                                  50
m12-L  TLTQSPTTLS  ASPGERVILS  CRASQSVSSS  HLAWYQQRPG  QTPRLLIYSS
m14-L  --TQSPGTLS  LSPGERATLS  CRASHSVSRA  YLAWYQQKPG  QAPRLLIYGT
m16-L  QMTQSPSSVS  ASVGDRVTIT  CRASQGISS.  WLAWYQQKPG  KAPKLLINAA
m18-L  QMTQSPSFLS  ASVGDRVSIT  CRASQDIQK.  FLAWYQLTPG  DAPKLLMYSA
       |             |            |            |          |
       |    FR1      |   CDR-L1   |    FR2     |          |
     51                                                 100
m12-L  SSRAAGIPDR  FSGSGSGTDF  TLTISRLEPE  DFAVYYCQNQ  GFSPRFFFGP
m14-L  SSRATGIPDR  FSGSGSGTDF  TLTISRLEPE  DFAVYYCQQY  GGSP..WFGQ
m16-L  SSLQSGVPSR  FSGSGSGTDF  TLTISSLQPE  DFATYYCQQA  NSFP.LTFGG
m18-L  STLQSGVPSR  FSGSGSGTEF  TLTISGLQPE  DFATYYCQHL  KRYP.YTFGQ

|              |                        |           |
       CDR-L2|         FR3                      CDR-L3       |

101                                                150
m12-L  GTTVDMKRTV  AAPSVFIFPP  SDEQLKSGTA  SVVCLLNNFY  PREAKVQWKV
m14-L  GTKVELKRTV  AAPSVFIFPP  SDEQLKSGTA  SVVCLLNNFY  PREAKVQWKV
m16-L  GTKVEIKRTV  AAPSVFIFPP  SDEQLKSGTA  SVVCLLNNFY  PREAKVQWKV
m18-L  GTKLEISRTV  AAPSVFIFPP  SDEQLKSGTA  SVVCLLNNFY  PREAKVQWKV

|            |
        FR4           |              CL 151                                                200
m12-L  DNALQSGNSQ  ESVTEQDSKD  STYSLSSTLT  LSKADYEKHK  VYACEVTHQL
m14-L  DNALQSGNSQ  ESVTEQDSKD  STYSLSSTLT  LSKADYEKHK  VYACEVTHQL
m16-L  DNALQSGNSQ  ESVTEQDSKD  STYSLSSTLT  LSKADYEKHK  VYACEVTHQL
m18-L  DNALQSGNSQ  ESVTEQDNKD  STYSLSSTLT  LSKADYEKHK  VYACEVTHQL 201         214
m12-L  LSSPVTKSFN  RGEC
m14-L  LSSPVTKSFN  RGEC
m16-L  LSSPVTKSFN  RGEC
m18-L  LSSPVTKSFN  RGEC
``` m12-L is SEQ ID NO: 5
m14-L is SEQ ID NO: 6
m16-L is SEQ ID NO: 7
m18-L is SEQ ID NO: 8

FIGURE 4

IDENTIFICATION OF NOVEL BROADLY CROSS-REACTIVE NEUTRALIZING HUMAN MONOCLONAL ANTIBODIES USING SEQUENTIAL ANTIGEN PANNING OF PHAGE DISPLAY LIBRARIES

CROSS-REFERENCE TO RELATED PATENT APPLICATIONS

This application is the U.S. national phase of International Patent Application No. PCT/US03/14292, which was filed on May 6, 2003, and which claims the benefit of U.S. Provisional Patent Application No. 60/378,408, which was filed on May 6, 2002.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 20,307 Byte ASCII (Text) file named "231481ST25," created on Jul. 2, 2007.

TECHNICAL FIELD OF THE INVENTION

The present invention relates to sequential antigen panning of phage display libraries (SAP; previously referred to as alternating antigen panning (AAP)) and its use to identify novel, broadly cross-reactive neutralizing antibodies, such as human monoclonal antibodies, and related fusion proteins, conjugates, nucleic acids, vectors, host cells; compositions, and methods of use.

BACKGROUND OF THE INVENTION

Binding of the HIV-1 envelope glycoprotein (Env, gp120-gp41) to CD4 and coreceptors initiates a series of conformational changes that are the heart of the fusion machinery leading to viral entry.[1] The elucidation of the nature of the Env conformational changes is not only a clue to the mechanism of HIV-1 entry but may also provide new tools for the development of inhibitors and vaccines.[2,3] It has been proposed that the interaction of coreceptor molecules with the Env-CD4 complex leads to intermediate Env conformations that may include structures conserved among various HIV-1 isolates that could be used as vaccines.[4,5] Of the four known potent broadly neutralizing antibodies (b12[7], 2F5[8,9], 2G12[10], and 4E10/Z13[11]), none have a receptor inducible epitope.

No single broadly cross-reactive monoclonal antibody against conformational receptor-inducible epitopes with potent neutralization activity for primary HIV isolates has been isolated and characterized. Typically, monoclonal antibodies against CD4-inducible epitopes such as 17b and CG10 are only weakly neutralizing against primary isolates[16] suggesting that CD4-inducible epitopes on gp120 may not serve as targets for potent broadly neutralizing antibodies.

It is an object of the present invention to provide a method for efficient selection of broadly cross-reactive antibodies termed SAP. The antibodies can be used, alone or in combination with other active agents or as fusion proteins or conjugates with other active agents, to inhibit, reduce the severity of, or treat an infection, such as with a bacterium, virus or parasite, or to inhibit cancer. This and other objects and advantages of the present invention, as well as additional inventive features, will become apparent from the detailed description provided herein.

BRIEF SUMMARY OF THE INVENTION

The present invention provides a method of selecting an antibody. The method comprises selecting an antibody from a phage display library using sequential antigen panning. In one embodiment, the method comprises a) selecting phage from a phage display library using a first selecting condition, wherein the first selecting condition is an antigen at a known concentration; and b) selecting phage from the phage selected in step a) using a second selecting condition, wherein the second selecting condition differs from the first selecting condition, with the proviso that this step can be repeated any number of times, each time using a different selecting condition, whereupon an antibody is selected from a phage display library. The present invention also provides a composition produced using such a method and a composition comprising a neutralizing antibody, wherein the antibody recognizes more than one strain of a pathogen.

In view of the above, the present invention provides an antibody to HIV envelope glycoprotein that can recognize one or more strains of HIV, wherein the epitope of HIV recognized by the antibody is inducible, and wherein the antibody comprises SEQ ID NO: 1, 2, 3, 4, 5, 6, 7, 8 or a variant of any of the foregoing, wherein the variant retains the ability to bind to the same epitope as that of SEQ ID NO: 1, 2, 3, 4, 5, 6, 7 or 8, respectively, to a greater or lesser extent. Also provided is a fusion protein or conjugate comprising such an antibody and a composition comprising the antibody, optionally in the form of a fusion protein or conjugate.

Also in view of the above, the present invention provides an isolated or purified nucleic acid molecule comprising the nucleotide sequence encoding the amino acid sequence of SEQ ID NO: 1, 2, 3, 4, 5, 6, 7, 8 or a variant of any of the foregoing, wherein the variant retains the ability to bind to the same epitope as that of SEQ ID NO: 1, 2, 3, 4, 5, 6, 7 or 8, respectively, to a greater or lesser extent. Also provided are a vector comprising such a nucleic acid molecule, a composition comprising the nucleic acid molecule, optionally in the form of a vector, and a host cell comprising the nucleic acid molecule, optionally in the form of a vector.

The present invention further provides methods of using the above nucleic acid molecules, vectors, host cells, antibodies, fusion proteins and conjugates. In one embodiment, the present invention provides a method of inhibiting an infection of an animal. In another embodiment, the present invention provides a method of reducing the severity of an infection in an animal. In yet another embodiment, the present invention provides a method of treating an infection of an animal. In still yet another embodiment, the present invention provides a method of inhibiting cancer in a mammal. The methods comprise administering to the animal an isolated or purified nucleic acid molecule encoding an above-described antibody, optionally as part of a fusion protein, wherein the nucleic acid molecule is optionally in the form of a vector and/or optionally contained within a cell, or the antibody, itself, optionally as part of a fusion protein or conjugate.

BRIEF DESCRIPTION OF THE FIGURES

FIG. 1 is a flow chart of sequential panning (m12 and m14).

FIG. 2 is a flow chart of sequential panning (m16 and m18).

FIG. 3 is the heavy chain Fd amino acid sequence alignment, in which FR indicates framework region, CDR indicates complementarity-determining region (also indicated in bold), and CH1 indicates first constant region of the heavy chain (SEQ ID NOS: 1-4).

FIG. 4 is the light chain amino acid sequence alignment, in which FR and CDR are as indicated for FIG. 3 and CL indicates constant region of light chain (SEQ ID NOS: 5-8).

DETAILED DESCRIPTION OF THE INVENTION

The present invention may be understood more readily by reference to the following detailed description of preferred embodiments of the invention and the Examples included therein and to the Figures and their previous and following description.

Before the present compounds, compositions, and/or methods are disclosed and described, it is to be understood that this invention is not limited to specific synthetic methods, specific recombinant biotechnology methods unless otherwise specified, or to particular reagents, pharmaceutical formulations or administration regimens unless otherwise specified, as such may, of course, vary. It is also to be understood that the terminology used herein is for the purpose of describing particular embodiments only and is not intended to be limiting.

It must be noted that, as used in the specification and the appended claims, the singular forms "a," "an" and "the" can include plural referents unless the context clearly dictates otherwise. Thus, for example, reference to "a compound" includes mixtures of compounds, reference to "a pharmaceutical carrier" includes mixtures of two or more such carriers, and the like.

In this specification and in the claims which follow, reference will be made to a number of terms, which shall be defined to have the following meanings:

Herein the term "sequential antigen panning" refers to a method of producing an antibody or antibodies comprising isolating the antibody or antibodies by screening a phage display library for antibodies that can bind to an antigen, wherein the isolation is continued by screening the binding antibodies for the ability to bind the antigen at a lower concentration or to bind an additional antigen, wherein this process can continue for two or more cycles, wherein the antibody or antibodies that bind on the last cycle are selected.

Herein the term "screening" refers to a method of isolating an antibody or antibodies from other antibodies, based on the level of binding activity to an antigen. An example of a screening method is a phage ELISA.

Herein the term "selecting" refers to a method of isolating an antibody or antibodies from other antibodies based on the ability to bind an antigen.

In view of the foregoing, the present invention provides a method of selecting an antibody. The method comprises selecting an antibody from a phage display library using sequential antigen panning. In one embodiment, the method comprises a) selecting phage from a phage display library using a first selecting condition, wherein the first selecting condition is an antigen at a known concentration; and b) selecting phage from the phage selected in step a) using a second selecting condition, wherein the second selecting condition differs from the first selecting condition, with the proviso that this step can be repeated any number of times, each time using a different selecting condition, whereupon an antibody is selected from a phage display library. The second selecting condition can differ from the first selecting condition in the antigen used, the concentration of the antigen used, or a combination of both. The method can further comprise c) selecting phage from the phage selected in step b) using a third selecting condition, wherein the third selecting condition differs from the first and second selecting conditions. The third seelcting condition can differ from the first and second selecting conditions in the antigen used, the concentration of the antigen used, or a combination of both. The method can further comprise d) selecting phage from the phage selected in step c) using a fourth selecting condition, wherein the fourth selecting condition differs from the first, second and third selecting conditions. The fourth selecting condition can differ from the first, second and third selecting conditions in the antigen used, the concentration of the antigen used, or a combination of both. The method can further comprise e) selecting phage from the phage selected in step d) using a fifth selecting condition, wherein the fifth selecting condition differs from the first, second, third and fourth selecting conditions. The fifth selecting condition can differ from the first, second, third and fourth selecting conditions in the antigen used, the concentration of the antigen used, or a combination of both. The method can further comprise f) selecting phage from the phage selected in step e) using a sixth selecting condition, wherein the sixth selecting condition differs from the first, second, third, fourth and fifth selecting conditions. The sixth selecting conditions can differ from the first, second, third, fourth and fifth selecting conditions in the antigen used, the concentration of the antigen used, or a combination of both.

In the context of the above method, the antigen can be an antigen from a bacterium, such as *M. tuberculosis, M. bovis, M. bovis* strain BCG, BCG substrains, *M. avium, M. intracellulare, M. africanum, M. kansasii, M. marinum, M. ulcerans, M. avium* subspecies *paratuberculosis, Nocardia asteroides,* other *Nocardia* species, *Legionella pneumophila,* other *Legionella* species, *Salmonella typhi,* other *Salmonella* species, *Shigella* species, *Yersinia pestis, Pasteurella haemolytica, Pasteurella multocida,* other *Pasteurella* species, *Actinobacillus pleuropneumoniae, Listeria monocytogenes, Listeria ivanovii, Brucella abortus,* other *Brucella* species, *Cowdria ruminantium, Chlamydia pneumoniae, Chlamydia trachomatis, Chlamydia psittaci, Coxiella burnetti,* other *Rickettsial* species, *Ehrlichia* species, *Staphylococcus aureus, Staphylococcus epidermidis, Streptococcus pyogenes, Streptococcus agalactiae, Bacillus anthracis, Escherichia coli, Vibrio cholerae, Campylobacter* species, *Neiserria meningitidis, Neiserria gonorrhea, Pseudomonas aeruginosa,* other *Pseudomonas* species, *Haemophilus influenzae, Haemophilus ducreyi,* other *Hemophilus* species, *Clostridium tetani,* other *Clostridium* species, *Yersinia enterolitica,* or other *Yersinia* species. Alternatively, the antigen can be an antigen from a parasite, such as *Toxoplasma gondii, Plasmodium falciparum, Plasmodium vivax, Plasmodium malariae,* other *Plasmodium* species, *Trypanosoma brucei, Trypanosoma cruzi, Leishmania major,* other *Leishmania* species, *Schistosoma mansoni,* other *Schistosoma* species, or *Entamoeba histolytica.* Alternatively, the antigen can be an antigen from a virus, such as Herpes simplex virus type-1, Herpes simplex virus type-2, Cytomegalovirus, Epstein-Barr virus, Varicella-zoster virus, Human herpesvirus 6, Human herpesvirus 7, Human herpesvirus 8, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A, Influenza virus B, Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Lymphocytic choriomeningitis virus, Rift Valley fever virus, Rotavirus A, Rotavirus B, Rotavirus C, Sindbis virus, Simian Immunodeficiency virus, human-cell leukemia virus type-1, Hantavirus, Rubella virus, human immunodeficiency virus type-1, or human immunodeficiency virus type-2. Alternatively, the antigen can be a tumor antigen, such as human epithelial cell mucin (Muc-1), the Ha-ras oncogene product, p53, carcino-embryonic antigen (CEA), the raf oncogene product, GD2, GD3, GM2, TF, sTn, MAGE-1, MAGE-3, BAGE, GAGE, tyrosinase, gp75, Melan-A/Mart-1, gp100, HER2/neu, EBV-LMP 1 & 2, HPV-F4, 6, 7, prostate-specific antigen (PSA), alpha-fetoprotein (AFP), CO17-1A, GA733, gp72, p53, the ras oncogene product, HPV E7, proteinase 3, HPV-16, MUM, Wilm's tumor antigen-1, telomerase, melanoma gangliosides, an antibody produced by a B cell tumor, a fragment of such an antibody, which contains an epitope of the idiotype of the antibody, a malignant B cell antigen receptor, a malignant B cell immunoglobulin idiotype, a variable region of an immunoglobulin, a hypervariable region or CDR of a variable region of an immunoglobulin, a malignant T cell receptor (TCR), or a variable region of a TCR and/or a hypervariable region of a TCR.

In the context of the above method, the antigen can be a non-protein antigen, a lipid, a nucleic acid, a peptide, or a protein. Specific examples of antigens include an antigen comprising gp140 or an antigen comprising gp120. Other examples include an antigen comprising CD4, CCR5 or CXCR4. An antigen comprising a complex of gp140 and CD4, an antigen comprising a complex of gp140, CD4 and CCR5, and an antigen comprising a complex of gp140, CD4 and CXCR4 are other examples.

The phage display library can comprise a phagemid vector comprising nucleic acid obtained from a source, such as bone marrow. The bone marrow can be from one or more HIV+ long-term nonprogressors or from one or more HIV exposed persistently seronegative individuals.

The sequential antigen panning methodology is useful for selecting cross-reactive antibodies against any antigen that shares common epitopes with other antigens. Examples include, but are not limited to, rapidly mutating viruses and cancer cells, as well as proteins that share common structural elements. It is anticipated that variations of this methodology can be devised, including strategies to use various antigens in different numbers and in alternative order during panning and screening.

An embodiment of the disclosed invention is the method of sequential antigen screening. The method of sequential antigen screening comprises a method of screening an antibody based on the ability to bind multiple antigens. This method comprises screening an antibody or antibodies for the ability to bind an antigen, selecting those antibodies that bind the antigen and repeating the screening using a antigen that differs from the previous antigen.

Throughout this application reference is made to various species of bacteria, virus, or parasites. It is an embodiement of the present invention that the listing of a species of organism comprises all strains of the species. For example, the bacterial species *Escherichia coli* comprises *E. coli* strains 0157: H7, 0126: H27, LMG 13580, LMG 15068 and 0126: H (see American Type Culture Collection, Rockville, Md.). Another example is Lymphocytic choriomeningitis virus, which comprises the Armstrong, c1-13, and WE strains (Field's Virology. Knipe and Howly eds. Philadelphia, Pa.: Lippincott Williams & Wilkins, 2001). In the present invention, HIV-1 is shown to comprise strain 89.6, HBX2, JRFL, and IIIB. It is clear that the SAP methods described herein can use an antigen or antigens of any of the known strains of any bacterium, or an antigen or antigens of any of the known strains of any virus, or an antigen or antigens of any of the known strains of any parasite.

In view of the above, the present invention also provides a composition produced using the above-described method. In one embodiment, the composition comprises a neutralizing antibody, wherein the antibody recognizes more than one strain of a pathogen. In another embodiment, the antibody is specific for a bacterium, such as those recited above, a parasite, such as those recited above, or a virus, such as those recited above, e.g., HIV, such as an antibody that recognizes conserved epitopes of HIV and can bind to one or more clade of HIV. Specific examples of an antibody include a neutralizing scFv antibody fragment and an Fab to HIV envelope glycoprotein that can recognize one or more strains of HIV, wherein the antibody comprises SEQ ID NO: 1, 2, 3, 4, 5, 6, 7, 8 or a variant of any of the foregoing, wherein the variant retains the ability to bind to the same epitope as that of SEQ ID NO: 1, 2, 3, 4, 5, 6, 7 or 8, respectfully, to a greater or lesser extent. While variants can be isolated from naturally occurring sources or be recombinantly produced, such variants also can be synthesized using standard peptide synthesizing techniques well-known to those of ordinary skill in the art (e.g., as summarized in Bodanszky, *Principles of Peptide Synthesis*, (Springer-Verlag, Heidelberg: 1984)). In particular, the polypeptide can be synthesized using the procedure of solid-phase synthesis (see, e.g., Merrifield, J. Am. Chem. Soc. 85: 2149-54 (1963); Barany et al., Int. J. Peptide Protein Res. 30: 705-739 (1987); and U.S. Pat. No. 5,424,398). If desired, this can be done using an automated peptide synthesizer. Removal of the t-butyloxycarbonyl (t-BOC) or 9-fluorenylmethyloxycarbonyl (Fmoc) amino acid blocking groups and separation of the polypeptide from the resin can be accomplished by, for example, acid treatment at reduced temperature. The polypeptide-containing mixture can then be extracted, for instance, with dimethyl ether, to remove non-peptidic organic compounds, and the synthesized polypeptide can be extracted from the resin powder (e.g., with about 25% w/v acetic acid). Following the synthesis of the polypeptide, further purification (e.g., using high performance liquid chromatography (HPLC)) optionally can be done in order to eliminate any incomplete polypeptides or free amino acids. Amino acid and/or HPLC analysis can be performed on the synthesized polypeptide to validate its identity. For other applications according to the invention, it may be preferable to produce the polypeptide as part of a larger fusion protein, such as by the methods described herein or other genetic means, or as part of a larger conjugate, such as through physical or chemical conjugation, as known to those of ordinary skill in the art and described herein.

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with the proteins disclosed herein. The antibodies can be tested for their desired activity using the in vitro assays described herein, or by analogous methods, after which their in vivo therapeutic and/or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567; and Morrison et al., *Proc. Natl. Acad. Sci. USA* 81: 6851-6855 (1984)).

The present inventive monoclonal antibodies can be made using any procedure which produces monoclonal antibodies. For example, monoclonal antibodies of the invention can be prepared using hybridoma methods, such as those described by Kohler and Milstein, *Nature*, 256:495 (1975). In a hybridoma method, a mouse or other appropriate host animal is typically immunized with an immunizing agent to elicit lymphocytes that produce antibodies that will specifically bind to the immunizing agent.

The monoclonal antibodies also can be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of antibodies). Libraries of antibodies or active antibody fragments also can be generated and screened using phage display techniques, e.g., as described in U.S. Pat. No. 5,804,440 to Burton et al. and U.S. Pat. No. 6,096,551 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in International Patent Application Publication No. WO 94/29348, published Dec. 22, 1994, and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

As used herein, the term "antibody or fragments thereof" encompasses chimeric antibodies and hybrid antibodies, with dual or multiple antigen or epitope specificities, single chain antibodies and fragments, such as F(ab')2, Fab', Fab, scFv and the like, including hybrid fragments. Thus, fragments of the antibodies that retain the ability to bind their specific antigens are provided. For example, fragments of antibodies which maintain HIV gp120 binding activity are included within the meaning of the term "antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York (1988)). Also included within the meaning of "antibody or fragments thereof" are conjugates of antibody fragments and antigen binding proteins (single chain antibodies) as described, for example, in U.S. Pat. No. 4,704,692, the contents of which are hereby incorporated by reference.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase bio-longevity, to alter secretory characteristics; etc. In any case, the antibody or antibody fragment must possess a bioactive property, such as specific binding to its cognate antigen. Functional or active regions of the antibody or antibody fragment can be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment (Zoller, M. J. *Curr. Opin. Biotechnol.* 3: 348-354 (1992)).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods of the invention serves to lessen the chance that an antibody administered to a human will evoke an undesirable immune response.

Human antibodies also can be prepared using any other technique. Examples of techniques for human monoclonal antibody production include those described by Cole et al. (*Monoclonal Antibodies and Cancer Therapy*, Alan R. Liss, p. 77 (1985)) and by Boerner et al. (*J. Immunol.* 147 (1): 86-95 (1991)). Human antibodies (and fragments thereof) also can be produced using phage display libraries (Hoogenboom et al., *J. Mol. Biol.* 227: 381 (1991); Marks et al., *J. Mol. Biol.* 222: 581 (1991)).

Human antibodies also can be obtained from transgenic animals. For example, transgenic, mutant mice that can produce a full repertoire of human antibodies in response to immunization have been described (see, e.g., Jakobovits et al., *Proc. Natl. Acad. Sci. USA* 90: 2551-255 (1993); Jakobovits et al., *Nature* 362: 255-258 (1993); and Bruggermann et al., *Year in Immunol.* 7: 33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge.

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., *Nature* 321: 522-525 (1986); Reichmann et al., *Nature* 332: 323-327 (1988); and Presta, *Curr. Opin. Struct. Biol.* 2: 593-596 (1992)).

Methods for humanizing non-human antibodies are well-known in the art. For example, humanized antibodies can be generated according to the methods of Winter and co-workers (Jones et al., *Nature* 321: 522-525 (1986); Riechmann et al., *Nature* 332: 323-327 (1988); and Verhoeyen et al., *Science* 239: 1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

A fusion protein or conjugate (conjugate produced by chemical or physical means) comprising an above-described antibody is also provided. The fusion protein or conjugate can comprise another antibody, such as one that binds to an epitope of HIV, such as a neutralizing scFv antibody fragment to HIV envelope glycoprotein that can recognize one or more strains of HIV, wherein the epitope of HIV recognized by the antibody is inducible. Alternatively, the fusion protein or conjugate can comprise CD4 or a toxin.

Toxins are poisonous substances produced by plants, animals, or microorganisms that, in sufficient dose, are often lethal. A preferred toxin is *Pseudomonas* toxin. Diphtheria toxin is a substance produced by *Corynebacterium diphtheria*, which can be used therapeutically. This toxin consists of an α subunit and a β subunit, which, under proper conditions, can be separated. Another example of a toxin is tetanus toxoid, which is produced by *Clostridium tetani*. Lectins are proteins, usually isolated from plant material, which bind to specific sugar moieties. Many lectins are also able to agglutinate cells and stimulate lymphocytes. However, ricin is a toxic lectin, which has been used immunotherapeutically. This is accomplished by binding the alpha-peptide chain of ricin, which is responsible for toxicity, to the antibody molecule to enable site-specific delivery of the toxic effect. Other therapeutic agents, which can be coupled to the antibodies, are known, or can be easily ascertained, by those of ordinary skill in the art.

Many peptide toxins have a generalized eukaryotic receptor binding domain; in these instances the toxin must be modified to prevent intoxication of cells not bearing the targeted receptor (e.g., to prevent intoxication of cells not bearing the "X" receptor but having a receptor for the unmodified toxin). Any such modifications must be made in a manner which preserves the cytotoxic functions of the molecule. Potentially useful toxins include, but are not limited to: cholera toxin, ricin, Shiga-like toxin (SLT-I, SLT-II, SLT-IIV), LT toxin, C3 toxin, Shiga toxin, pertussis toxin, tetanus toxin, *Pseudomonas* exotoxin, alorin, saporin, modeccin, and gelanin. Diphtheria toxin can be used to produce molecules useful as described herein. Diphtheria toxin, whose sequence is known, and hybrid molecules thereof, are described in detail in U.S. Pat. No. 4,675,382 to Murphy. The natural diphtheria toxin molecule secreted by *Corynebacterium diphtheriae* consists of several functional domains which can be characterized, starting at the amino terminal end of the molecule, as enzymatically-active Fragment A (amino acids Gly1-Arg193) and Fragment B (amino acids Ser194-Ser535), which includes a translocation domain and a generalized cell binding domain (amino acid residues 475 through 535). The process by which diphtheria toxin intoxicates sensitive eukaryotic cells involves at least the following steps: (i) the binding domain of diphtheria toxin binds to specific receptors on the surface of a sensitive cell; (ii) while bound to its receptor, the toxin molecule is internalized into an endocytic vesicle; (iii) either prior to internalization, or within the endocytic vesicle, the toxin molecule undergoes a proteolytic cleavage between fragments A and B; (iv) as the pH of the endocytic vesicle decreases to below 6, the toxin crosses the endosomal membrane, facilitating the delivery of Fragment A into the cytosol; (v) the catalytic activity of Fragment A (i.e., the nicotinamide adenine dinucleotide-dependent adenosine diphosphate (ADP) ribosylation of the eukaryotic protein synthesis factor termed "Elongation Factor 2") causes the death of the intoxicated cell. A single molecule of Fragment A introduced into the cytosol is sufficient to inhibit the cell's protein synthesis machinery and kill the cell. The mechanism of cell killing by *Pseudomonas* exotoxin A, and possibly by certain other naturally-occurring toxins, is very similar.

A mixed toxin molecule is a molecule derived from two different polypeptide toxins. Generally, as discussed above in connection with diphtheria toxin, polypeptide toxins have, in addition to the domain responsible for generalized eukaryotic cell binding, an enzymatically active domain and a translocation domain. The binding and translocation domains are required for cell recognition and toxin entry respectively. Naturally-occurring proteins which are known to have a translocation domain include diphtheria toxin, *Pseudomonas* exotoxin A, and possibly other peptide toxins. The translocation domains of diphtheria toxin and *Pseudomonas* exotoxin A are well characterized (see, e.g., Hoch et al., Proc. Natl. Acad. Sci. USA 82:1692, 1985; Colombatti et al., *J. Biol. Chem.* 261: 3030 (1986); and Deleers et al., *FEBS Lett.* 160: 82 (1983)), and the existence and location of such a domain in other molecules may be determined by methods such as those employed by Hwang et al. (Cell 48:129 (1987)); and Gray et al. (*PNAS USA* 81: 2645 (1984)). A useful mixed toxin hybrid molecule can be formed by fusing the enzymatically active A subunit of *E. coli* Shiga-like toxin (Calderwood et al., *PNAS USA* 84: 4364 (1987)) to the translocation domain (amino acid residues 202 through 460) of diphtheria toxin, and to a molecule targeting a particular cell type, as described in U.S. Pat. No. 5,906,820 to Bacha. The targeting portion of the three-part hybrid causes the molecule to attach specifically to the targeted cells, and the diphtheria toxin translocation portion acts to insert the enzymatically active A subunit of the Shiga-like toxin into the targeted cell. The enzymatically active portion of Shiga-like toxin, like diphtheria toxin, acts on the protein synthesis machinery of the cell to prevent protein synthesis, thus killing the cell.

The targeting molecule (for example, the antibody), and the cytotoxin can be linked in several ways. If the hybrid molecule is produced by expression of a fused gene, a peptide bond serves as the link between the cytotoxin and the antibody or antibody fragment. Alternatively, the toxin and the binding ligand can be produced separately and later coupled by means of a non-peptide covalent bond. For example, the covalent linkage may take the form of a disulfide bond. In this case, the DNA encoding the antibody can be engineered to contain an extra cysteine codon. The cysteine must be positioned so as to not interfere with the binding activity of the molecule. The toxin molecule must be derivatized with a sulfhydryl group reactive with the cysteine of the modified antibody. In the case of a peptide toxin this can be accomplished by inserting a cysteine codon into the DNA sequence encoding the toxin. Alternatively, a sulfhydryl group, either by itself or as part of a cysteine residue, can be introduced using solid phase polypeptide techniques. For example, the introduction of sulfhydryl groups into peptides is described by Hiskey (*Peptides* 3: 137 (1981)). The introduction of sulfhydryl groups into proteins is described in Maasen et al. (*Eur. J. Biochem.* 134: 32 (1983)). Once the correct sulfhydryl groups are present, the cytotoxin and antibody are purified, both sulfur groups are reduced; cytotoxin and ligand are mixed; (in a ratio of about 1:5 to 1:20) and disulfide bond formation is allowed to proceed to completion (generally 20 to 30 minutes) at room temperature. The mixture is then dialyzed against phosphate buffered saline or chromatographed in a resin such as Sephadex to remove unreacted ligand and toxin molecules.

Numerous types of cytotoxic compounds can be joined to proteins through the use of a reactive group on the cytotoxic compound or through the use of a cross-linking agent. A common reactive group that will form a stable covalent bond in vivo with an amine is isothiocyanate (Means et al., *Chemical Modifications of Proteins*, Holden-Day, San Francisco (1971), pp. 105-110). This group preferentially reacts with the ε-amine group of lysine. Maleimide is a commonly used reactive group to form a stable in vivo covalent bond with the sulfhydryl group on cysteine (Ji, *Methods Enzymol.* 91: 580-609 (1983)). Monoclonal antibodies are incapable of forming covalent bonds with radiometal ions, but they can be attached to the antibody indirectly through the use of chelating agents that are covalently linked to the antibodies. Chelating agents can be attached through amines (Meares et al., *Anal. Biochem.* 142: 68-78 (1984)) and sulfhydryl groups (Koyama, *Chem. Abstr.* 120: 217262t (1994)) of amino acid residues and also through carbohydrate groups (Rodwell et al., *Proc. Natl. Acad. Sci.* 83: 2632-2636 (1986); Quadri et al., *Nucl. Med. Biol.* 20: 559-570 (1993)). Since these chelating agents contain two types of functional groups, one to bind metal ions and the other to joining the chelate to the antibody, they are commonly referred as bifunctional chelating agents (Sundberg et al., *Nature* 250: 587-588 (1974)).

Crosslinking agents have two reactive functional groups and are classified as being homo or heterobifunctional. Examples of homobifunctional crosslinking agents include bismaleimidohexane (BMW, which is reactive with sulfhydryl groups (Chen et al., *J. Biol. Chem.* 266: 18237-18243 (1991)), and ethylene glycolbis[succinimidylsucciate] (EGS), which is reactive with amino groups (Browning et al., *J. Immunol.* 143: 1859-1867 (1989)). An example of a heterobifunctional crosslinker is -maleimidobenzoyl-N-hydroxysuccinimide ester (MBS) (Myers et al., *J. Immunol. Meth.* 21: 129-142 (1989)). These methodologies are simple and are commonly employed.

The antibodies and antibody fragments of the invention can be used to identify and/or inactivate cancer cells that are dependent on the proteins involved in the disclosed pathogenic processes in vitro or in vivo. Although described primarily with reference to radioisotopes, especially indium ("In"), which is useful for diagnostic purposes, and yttrium ("Y"), which is cytotoxic, other substances which harm or inactivate cancer cells can be substituted for the radioisotope. The antibodies or substrate analogs may be unlabeled or labeled with a therapeutic agent. These agents can be coupled either directly or indirectly to the disclosed antibodies or substrate analogs. One example of indirect coupling is by use of a spacer moiety. These spacer moieties, in turn, can be either insoluble or soluble (wiener, et al., Science, 231:148, 1986) and can be selected to enable drug release from the antibodies or substrate analogs at the target site. Examples of therapeutic agents which can be coupled to the disclosed antibodies or substrate analogs are drugs, radioisotopes, lectins, and toxins or agents which will covalently attach the antibody or substrate analog to the mema.

Certain isotypes may be more preferable than others depending on such factors as distribution as well as isotype stability and emission. In general, alpha and beta particle-emitting radioisotopes are preferred in immunotherapy. Preferred are short range, high energy alpha emitters such as $^{212}$Bi. Examples of radioisotopes which can be bound to the disclosed antibodies for therapeutic purposes are. $^{125}$I, $^{131}$I, $^{90}$Y, $^{67}$Cu, $^{212}$Bi, $^{211}$At, $^{212}$Pb, $^{47}$Sc, $^{109}$Pd, and $^{188}$Re.

The radioisotopes are preferred since they are small and well characterized, and can be used as diagnostics and followed after administration using standard non-invasive radio-imaging techniques.

As radioisotopes decay, they emit characteristic photons or particles or both. Photons, commonly referred to as gamma rays, are penetrating. If their energy level is high enough, they can travel through the body and be detected by diagnostic instrumentation. Radioisotopes that emit photons can be attached to an antibody or substrate analog and used for diagnostic imaging. This application is termed radioimmunoscintigraphy (RIS). The shorter the distance between the antigen and the target, the shorter the required range of emission of the radioisotope. Auger electrons have a very short path length (5-10 nm) and need to be internalized to be cytotoxic (Adelstein, et al., *Nucl. Med. Biol.* 14:165-169 (1987)). Only antibodies or substrate analogs that are internalized after binding to a cell should be considered for radioisotopes that emit Auger electrons. Alpha particles need to be close to a cell (within 3-4 cell diameters) to be effective (Vriesendorp, et al., Radioimmunoglobulin therapy. In: High Dose Cancer Therapy. Armitage et al. (eds)., (Williams & Wilkins, Baltimore, Md. 1992) pp. 84-123). Both Auger electrons and alpha emitters have high selectivity because their short-range emission will not irradiate neighboring normal cells.

The radiometals $^{111}$In and $^{90}$Y are, respectively, pure γ- and pure β-emitters. Iodine-125, the most commonly used emitter of Auger electrons, has a half-life of 60 days and frequently is released by the immunoconjugate in vivo (dehalogenation) (Vriesendorp, et al., 1992). The most commonly considered alpha emitters for clinical use, astatine-211 and bismuth-212, have short half-lives (7.2 h and 1.0 h, respectively) and decay into radioactive isotopes, that may not be retained by the immunoconjugate after the first alpha emission (Wilbur, *Antibiot. Immunoconjug. Radiopharm.* 4:85-97 (1991)). The use of an immunoconjugate radiolabeled with $^{111}$In has been proposed to predict the behavior of the poorly imageable $^{90}$Y-labeled immunoconjugate (Korngold, et al., *Cancer Res.* 20:1488-1494 (1960); Welt, et al., *J. Clin. Oncol.* 12:1561-1571 (1994); Breitz, et al., *J. Nucl. Med.* 33:1099-1112 (1992); Vriesendorp, et al., *Cancer Res.* (suppl) 55:5888s-5892s (1995)). Previous studies using stable radiometal chelation have demonstrated similar biodistributions for radioimmunoconjugates labeled with $^{111}$In and $^{90}$Y (Welt, et al., *J. Clin. Oncol.* 12:1561-1571 (1994); Breitz, et al., *J. Nucl. Med.* 33:1099-1112 (1992)).

For diagnostic administration, the immunoconjugate would be radiolabeled with a pure gamma-emitting radioisotope like indium-111 ($^{111}$In) or technetium-99m ($^{99m}$Tc). Both of these isotopes emit gamma rays within the appropriate energy range for imaging, (100-250 keV). Energies below this range are not penetrating enough to reach an external imaging device. Higher energy levels are difficult to collimate and provide diagnostic images with poor resolution. The short-half life of $^{99m}$Tc restricts its use to immunoconjugates with rapid tumor uptake. The use of $^{111}$In-labeled immunoconjugate has been proposed to predict the in vivo behavior of an immunoconjugate radiolabeled with $^{90}$Y, a pure beta-emitter, since they have similar half-lives and comparable chelation chemistry (Vriesendorp, et al., *Cancer. Res.* (suppl) 55:5888s-5892s (1995); Vriesendorp, et al., Radioimmunoglobulin therapy. 1992); DeNardo, et al., *J. Nucl. Med.* 36:829-836 (1995); Leichner, et al., *Int. J. Radiat. Oncol. Biol. Phys.* 14:1033-1042 (1988)). An advantage of using two separate radioisotopes, one for imaging and one for therapy, is that it allows for outpatient treatment. The low amount of radioactivity used diagnostically does not represent a radiation hazard, while the radiation emitted by a therapeutic pure beta-emitter will largely be absorbed in the vicinity of the targeted cells. This treatment scheme is dependent on similar pharmacokinetics for both radiolabeled reagents and requires a stable means of attaching both radioactive compounds to the antibody.

Some radioisotopes can be attached directly to the antibody; others require an indirect form of attachment. The radioisotopes $^{125}$I, $^{131}$I, $^{99m}$Tc, $^{186}$Re and $^{188}$Re can be covalently bound to proteins (including antibodies) through amino acid functional groups. For radioactive iodine it is usually through the phenolic group found on tyrosine. There are numerous methods to accomplish this: chloramine-T (Greenwood, et al. *Biochem J.* 89: 114-123 (1963)); and Iodogen (Salacinski, et al. *Anal. Biochem.* 117: 136-146 (1981)). Tc and Re can be covalently bound through the sulfhydryl group of cysteine (Griffiths, et al. *Cancer Res.* 51: 4594-4602 (1991)). The problem with most of the techniques is that the body has efficient methods to break these covalent bonds, releasing the radioisotopes back into the circulatory system. Generally, these methods are acceptable for imaging purposes ($^{99m}$Tc), but not for therapeutic purposes.

The present invention provides an isolated or purified nucleic acid molecule comprising the nucleotide sequence encoding the amino acid sequence of SEQ ID NO: 1, 2, 3, 4, 5, 6, 7, 8 or a variant of any of the foregoing, wherein the variant retains the ability to bind to the same epitope as that of SEQ ID NO: 1, 2, 3, 4, 5, 6, 7 or 8, respectfully, to a greater or lesser extent. The term "isolated" as used herein means having been removed from its natural environment. The term "purified" as used herein means having been increased in purity, wherein "purity" is a relative term, and not to be construed as absolute purity. The term "nucleic acid molecule" as used herein means a polymer of DNA or RNA, (i.e., a polynucleotide), which can be single-stranded or double-stranded, synthesized or obtained from natural sources, and which can contain natural, non-natural or altered nucleotides. Such nucleic acid molecules can be synthesized in accordance with methods well-known in the art.

The nucleic acid molecule encoding a variant can comprise one or more mutations. By "mutation" is meant any insertion, deletion, substitution and/or inversion in a given oligonucleotide. Such mutated oligonucleotides and fragments thereof can be obtained from naturally occurring sources or generated using methods known in the art. For instance, site-specific mutations can be introduced by ligating into an expression vector a synthesized oligonucleotide comprising the mutation(s). Alternately, oligonucleotide-directed site-specific mutagenesis procedures can be used, such as disclosed in Walder et al., Gene 42: 133 (1986); Bauer et al., Gene 37: 73 (1985); Craik, Biotechniques, 12-19 (January 1995); and U.S. Pat. Nos. 4,518,584 and 4,737,462. A preferred means for introducing mutations is the QuikChange Site-Directed Mutagenesis Kit (Stratagene, LaJolla, Calif.). While the above-described mutated oligonucleotides and fragments thereof can be generated in vivo and then isolated or purified, alternatively, they can be synthesized. A variety of techniques used to synthesize the oligonucleotides and fragments thereof of the present invention are known in the art. See, for example, Lemaitre et al., *Proceedings of the National Academy of the Sciences* 84: 648-652 (1987) and the references cited herein under "EXAMPLES." The oligonucleotides and fragments thereof of the present invention can alternatively be synthesized by companies, such as Eurogentec, Belgium. Preferably, the nucleotides encoding CDRH3 remain unchanged (see, e.g., FIGS. 3 and 4) or are only slightly changed, such as by conservative or neutral amino acid substitution(s). Mutations can be tolerated elsewhere. Activity of the encoded antibody can be assess in vitro under physiological conditions.

A vector comprising any of the above-described isolated or purified nucleic acid molecules, or fragments thereof, is further provided by the present invention. Any of the above nucleic acid molecules, or fragments thereof, can be cloned into any suitable vector and can be used to transform or transfect any suitable host. The selection of vectors and methods to construct them are commonly known to persons of ordinary skill in the art and are described in general technical references (see, in general, "Recombinant DNA Part D," *Methods in Enzymology*, Vol. 153, Wu and Grossman, eds., Academic Press (1987)). Desirably, the vector comprises regulatory sequences, such as transcription and translation initiation and termination codons, which are specific to the type of host (e.g., bacterium, fungus, plant or animal) into which the vector is to be introduced, as appropriate and taking into consideration whether the vector is DNA or RNA. Preferably, the vector comprises regulatory sequences that are specific to the genus of the host. Most preferably, the vector comprises regulatory sequences that are specific to the species of the host.

Constructs of vectors, which are circular or linear, can be prepared to contain an entire nucleic acid sequence as described above or a portion thereof ligated to a replication system functional in a prokaryotic or eukaryotic host cell. Replication systems can be derived from ColE1, 2 mμ plasmid, λ, SV40, bovine papilloma virus, and the like.

In addition to the replication system and the inserted nucleic acid, the construct can include one or more marker genes, which allow for selection of transformed or transfected hosts. Marker genes include biocide resistance, e.g., resistance to antibiotics, heavy metals, etc., complementation in an auxotrophic host to provide prototrophy, and the like.

Suitable vectors include those designed for propagation and expansion or for expression or both. A preferred cloning vector is selected from the group consisting of the pUC series, the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI101, pBI101.2, pBI101.3, pBI121 and pBIN19 (Clontech). Examples of animal expression vectors include pEUK- C1, pMAM and pMAMneo (Clontech). The TOPO cloning system (Invitrogen, Carlsbad, Calif.) also can be used in accordance with the manufacturer's recommendations.

An expression vector can comprise a native or normative promoter operably linked to an isolated or purified nucleic acid molecule as described above. The selection of promoters, e.g., strong, weak, inducible, tissue-specific and developmental-specific, is within the skill in the art. Similarly, the combining of a nucleic acid molecule, or fragment thereof, as described above with a promoter is also within the skill in the art.

Suitable viral vectors include, for example, retroviral vectors, parvovirus-based vectors, e.g., adeno-associated virus (AAV)-based vectors, AAV-adenoviral chimeric vectors, and adenovirus-based vectors, and lentiviral vectors, such as Herpes simplex (HSV)-based vectors. These viral vectors can be prepared using standard recombinant DNA techniques described in, for example, Sambrook et al., *Molecular Cloning, a Laboratory Manual*, 2d edition, Cold Spring Harbor Press, Cold Spring Harbor, N.Y. (1989); and Ausubel et al., *Current Protocols in Molecular Biology*, Greene Publishing Associates and John Wiley & Sons, New York, N.Y. (1994).

A retroviral vector is derived from a retrovirus. Retrovirus is an RNA virus capable of infecting a wide variety of host cells. Upon infection, the retroviral genome integrates into the genome of its host cell and is replicated along with host cell DNA, thereby constantly producing viral RNA and any nucleic acid sequence incorporated into the retroviral genome. As such, long-term expression of a therapeutic factor(s) is achievable when using retrovirus. Retroviruses contemplated for use in gene therapy are relatively non-pathogenic, although pathogenic retroviruses exist. When employing pathogenic retroviruses, e.g., human immunodeficiency virus (HIV) or human T-cell lymphotrophic viruses (HTLV), care must be taken in altering the viral genome to eliminate toxicity to the host. A retroviral vector additionally can be manipulated to render the virus replication-deficient. As such, retroviral vectors are considered particularly useful for stable gene transfer in vivo. Lentiviral vectors, such as HIV-based vectors, are exemplary of retroviral vectors used for gene delivery. Unlike other retroviruses, HIV-based vectors are known to incorporate their passenger genes into non-dividing cells and, therefore, can be of use in treating persistent forms of disease.

AAV vectors are viral vectors of particular interest for use in gene therapy protocols. AAV is a DNA virus, which is not known to cause human disease. The AAV genome is comprised of two genes, rep and cap, flanked by inverted terminal repeats (ITRs), which contain recognition signals for DNA replication and packaging of the virus. AAV requires co-infection with a helper virus (i.e., an adenovirus or a Herpes simplex virus), or expression of helper genes, for efficient replication. AAV can be propagated in a wide array of host cells including human, simian, and rodent cells, depending on the helper virus employed. An AAV vector used for administration of a nucleic acid sequence typically has approximately 96% of the parental genome deleted, such that only the ITRs remain. This eliminates immunologic or toxic side effects due to expression of viral genes. If desired, the AAV rep protein can be co-administered with the AAV vector to enable integration of the AAV vector into the host cell genome. Host cells comprising an integrated AAV genome show no change in cell growth or morphology (see, e.g., U.S. Pat. No. 4,797,368). As such, prolonged expression of therapeutic factors from AAV vectors can be useful in treating persistent and chronic diseases.

Optionally, the isolated or purified nucleic acid molecule, or fragment thereof, upon linkage with another nucleic acid molecule, can encode a fusion protein. The generation of fusion proteins is within the ordinary skill in the art and can involve the use of restriction enzyme or recombinational cloning techniques (see, e.g., Gateway™ (Invitrogen)). See, also, U.S. Pat. No. 5,314,995.

In view of the foregoing, the present invention also provides a composition comprising an above-described isolated or purified nucleic acid molecule, optionally in the form of a vector. The composition can comprise other components as described further herein.

Also in view of the above, the present invention provides a host cell comprising an above-described isolated or purified nucleic acid molecule, optionally in the form of a vector. It is most preferable that the cell of the present invention expresses the vector, such that the oligonucleotide, or fragment thereof, is both transcribed and translated efficiently by the cell. Examples of cells include, but are not limited to, a human cell, a human cell line, *E. coli* (e.g., *E. coli* TB-1, TG-2, DH5α, XL-Blue MRF' (Stratagene), SA2821 and Y1090), *B. subtilis, P. aerugenosa, S. cerevisiae, N. crassa*, insect cells (e.g., Sf9, Ea4) and others set forth herein below. The host cell can be present in a host, which can be an animal, such as a mammal, in particular a human.

The host cell can be isolated from or in an animal, such as a mammal, e.g., a mouse, rat, rabbit, cow, sheep, pig, primate, or human. In this regard, an above-described nucleic acid molecule, optionally in the form of a vector, can be introduced into a stem cell. The stem cell can then be implanted into an animal, such as a mammal, e.g., a female. While an above-described nucleic acid molecule, optionally in the form of a vector, can be introduced into any cell in an animal, preferably the cell is a B lymphocyte, such that 5-10%, 10-20%, 20-30%, 30-40%, 40-50%, 50-60%, 60-70%, 70-80%, 80-90% or 90-100% of the B cells are specific for a given antigen.

The above nucleic acid molecules, vectors, host cells, antibodies, fusion proteins and conjugtes are preferably administered to a subject as a composition, such as one comprising a pharmaceutically acceptable carrier. By "pharmaceutically acceptable" is meant a material that is not biologically or otherwise undesirable, i.e., the material can be administered to a subject without causing any undesirable biological effects or interacting in a deleterious manner with any of the other components of the pharmaceutical composition in which it is contained. The carrier is selected to minimize any degradation of the active ingredient and to minimize any adverse side effects in the subject. Suitable carriers and their formulations are described in *Remington: The Science and Practice of Pharmacy* (19th ed.), A. R. Gennaro, ed., Mack Publishing Company, Easton, Pa. (1995), and include carriers, thickeners, diluents, buffers, preservatives, surface-active agents, and the like, in addition to the active agent. The pharmaceutical composition also can comprise one or more active ingredients, such as antimicrobial agents, anti-inflammatory agents, anesthetics, and the like. Typically, an appropriate amount of a pharmaceutically acceptable salt is used in the formulation to render the formulation isotonic. Examples of pharmaceutically acceptable carriers include, but are not limited to, saline, Ringer's solution and dextrose solution. The pH of the solution is preferably from about 5 to about 8, and more preferably from about 7 to about 7.5. Further carriers include sustained-release preparations, such as semipermeable matrices of solid hydrophobic polymers containing the antibody, which matrices are in the form of shaped articles, e.g., films, liposomes or microparticles. It will be apparent to those persons skilled in the art that certain carriers can be preferable depending upon, for instance, the route of administration and concentration of antibody being administered.

The above nucleic acid molecules, vectors, host cells, antibodies, fusion proteins and conjugates can be administered to a human or a collection of cells by injection (e.g., transdermal, intravenous, intraperitoneal, subcutaneous, intramuscular), or by other methods, such as infusion, that ensure delivery to the bloodstream in an effective form. Local or intravenous injection is preferred. Other methods include topical, such as topical intranasal administration or administration by inhalant, vaginal, rectal, ophthalmic, oral, intravenous drop, subcutaneous, and the like.

As used herein, "topical intranasal administration" means delivery of the compositions into the nose and nasal passages through one or both of the nares and can comprise delivery by a spraying mechanism or droplet mechanism, or through aerosolization. Delivery also can be directly to any area of the respiratory system (e.g., lungs) via intubation.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives also can be present such as, for example, antimicrobials, antioxidants, chelating agents, inert gases and the like.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves the use of a slow-release or sustained-release system such that a constant dosage is maintained. See, e.g., U.S. Pat. No. 3,610,795, which is incorporated by reference herein.

The composition (for example, incorporated into microparticles, liposomes, or cells) can be targeted to a particular cell type via antibodies, receptors, or receptor ligands. The following references are examples of the use of this technology to target specific proteins to tumor tissue (Senter et al., Bioconjugate Chem. 2: 447-451 (1991); Bagshawe, Br. J. Cancer 60: 275-281 (1989); Bagshawe et al., Br. J. Cancer 58: 700-703 (1988); Senter et al., Bioconjugate Chem. 4:3-9 (1993); Battelli et al., Cancer Immunol. Immunother. 35: 421-425 (1992); Pietersz and McKenzie, Immunolog. Reviews 129: 57-80 (1992); and Roffler et al., Biochem. Pharmacol 42: 2062-2065 (1991)). Vehicles, such as "stealth" and other antibody-conjugated liposomes (including lipid-mediated drug targeting), receptor-mediated targeting of DNA through cell specific ligands, lymphocyte-directed tumor targeting, and highly specific therapeutic retroviral targeting of cells in vivo, can be used. The following references are examples of the use of this technology to target specific proteins to tissue (Hughes et al., Cancer Research 49: 6214-6220 (1989); and Litzinger and Huang, Biochimica et Biophysica Acta 1104: 179-187 (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis have been reviewed (Brown and Greene, DNA and Cell Biology 10 (6): 399-409 (1991)).

Formulations for topical administration may include ointments, lotions, creams, gels, drops, suppositories, sprays, liquids and powders. Conventional pharmaceutical carriers, aqueous, powder or oily bases, thickeners and the like can be necessary or desirable.

Compositions for oral administration include powders or granules, suspensions or solutions in water or non-aqueous media, capsules, sachets, or tablets. Thickeners, flavorings, diluents, emulsifiers, dispersing aids or binders can be desirable.

Some of the compositions potentially can be administered as a pharmaceutically acceptable acid- or base-addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, ammonium hydroxide, and potassium hydroxide, and organic bases, such as mono-, di-, trialkyl and aryl amines and substituted ethanolamines.

Effective dosages and schedules for administering the above nucleic acid molecules, vectors, host cells, antibodies, and fusion proteins can be determined empirically, and making such determinations is within the skill in the art. Those skilled in the art will understand that the dosage that must be administered will vary depending on, for example, the subject, the route of administration, whether a nucleic acid molecule, vector, host cell, antibody, fusion protein or conjugate is being administered, and whether other drugs being administered, not to mention the age, condition, and gender of the human and the extent of disease. Guidance in selecting appropriate doses for antibodies (or fusion proteins comprising same) is found in the literature on therapeutic uses of antibodies, e.g., Handbook of Monoclonal Antibodies, Ferrone et al., eds., Noges Publications, Park Ridge, N.J. (1985), Ch. 22 and pp. 303-357; Smith et al., Antibodies in Human Diagnosis and Therapy, Haber et al., eds., Raven Press, New York (1977), pp. 365-389. A typical daily dosage of the antibody used alone can range from about 1 µg/kg up to about 100 mg/kg of body weight or more per day, depending on the factors mentioned above. For example, the range can be from about 100 mg to one gram per dose. Nucleic acids, vectors and host cells should be administered so as to result in comparable levels of production of antibodies or fusion proteins thereof.

Following administration of a nucleic acid molecule, vector, host cell, antibody, fusion protein or conjugate for treating, inhibiting, or reducing the severity of an HIV infection, the efficacy of the therapeutic agent can be assessed in various ways well-known to the skilled practitioner. For instance, one of ordinary skill in the art will understand that an antibody of the invention is efficacious in treating or inhibiting an HIV infection in a subject by observing that the antibody reduces viral load or prevents a further increase in viral load. Viral loads can be measured by methods that are known in the art, for example, using polymerase chain reaction assays to detect the presence of HIV nucleic acid or antibody assays to detect the presence of HIV protein in a sample (e.g., but not limited to, blood) from a subject or patient, or by measuring the level of circulating anti-HIV antibody levels in the patient. Efficacy of the antibody treatment also can be determined by measuring the number of CD4$^+$ T cells in the HIV-infected subject. An antibody treatment that inhibits an initial or further decrease in CD4$^+$ T cells in an HIV-positive subject or patient, or that results in an increase in the number of CD4$^+$ T cells in the HIV-positive subject, is an efficacious antibody treatment.

The nucleic acid molecules, vectors, host cells, antibodies, fusion proteins and/or conjugates of the invention can be administered prophylactically to patients or subjects who are at risk for being exposed to HIV or who have been newly exposed to HIV. In subjects who have been newly exposed to HIV but who have not yet displayed the presence of the virus (as measured by PCR or other assays for detecting the virus) in blood or other body fluid, efficacious treatment with an antibody of the invention partially or completely inhibits the appearance of the virus in the blood or other body fluid.

The nucleic acid molecules, vectors, host cells, antibodies, fusion proteins and/or conjugates of the invention can be combined with other well-known therapies and prophylactic vaccines already in use. Such combinations can generate an additive or a synergistic effect with current treatments. The nucleic acid molecules, vectors, hsot cells, antibodies and/or conjugates of the invention can be combined with HIV and AIDS therapies and vaccines such as highly active antiretroviral therapy (HAART), AZT, structured treatment interruptions of HAART, cytokine immune enhancement therapy (IL-2, IL-12, CD40L+IL-12, IL-7, IFNs), cell replacement therapy, recombinant viral vector vaccines, DNA vaccines, inactivated virus preparations, and immunosuppressive agents, such as Cyclosporin A. Such therapies can be administered in the manner already in use for the known treatment providing a therapeutic or prophylactic effect (Silvestri and Feinberg "immune Intervention in AIDS." In *Immunology of Infectious Disease*. H. E. Kauffman, A. Sher, and R. Ahmed eds., ASM Press. Washington D.C. (2002)).

As described above, the compositions can be administered in a pharmaceutically acceptable carrier and can be delivered to the subject's cells in vivo and/or ex vivo by a variety of mechanisms well-known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well-known in the art. Compositions comprising a nucleic acid, optionally in the form of a vector encoding the antibody or fusion protein comprising same, can be introduced into the cells via any gene transfer mechanism, such as, for example, calcium phosphate mediated gene delivery, electroporation, microinjection or proteoliposomes. The transduced cells then can be infused (e.g., in a pharmaceutically acceptable carrier) or homotopically transplanted back into the subject per standard methods for the cell or tissue type. Standard methods are known for transplantation or infusion of various cells into a subject.

In view of the above, the present invention provides a method of inhibiting an infection in an animal. The method comprises administering to the animal an infection-inhibiting amount of a composition comprising an antibody produced according to the above method, optionally in the form of a fusion protein, wherein the antibody or fusion protein thereof is optionally encoded in an isolated or purified nucleic acid molecule, which is optionally in the form of a vector and/or optionally contained within a cell, whereupon the infection in the animal is inhibited. The infection can be with a bacterium, such as one of those described above, a parasite, such as one of those described above, or a virus, such as one of those described above.

The present invention also provides a method of reducing the severity of an infection in an animal. The method comprises administering to the animal a severity of infection-reducing amount of a composition comprising an antibody produced according to the above method, optionally in the form of a fusion protein, wherein the antibody or fusion protein thereof is optionally encoded in an isolated or purified nucleic acid molecule, which is optionally in the form of a vector and/or optionally contained within a cell, whereupon the severity of the infection in the animal is reduced. The infection can be with a bacterium, such as one of those described above, a parasite, such as one of those described above, or a virus, such as one of those described above.

The present invention further provides a method of treating an infection of an animal. The method comprises administering to the animal an infection-treating amount of a composition comprising an antibody produced according to the above method, optionally in the form of a fusion protein, wherein the antibody or fusion protein thereof is optionally encoded in an isolated or purified nucleic acid molecule, which is optionally in the form of a vector and/or optionally contained within a cell, whereupon the infection of the animal is treated. The infection can be with a bacterium, such as one of those described above, a parasite, such as one of those described above, or a virus, such as one of those described above.

The present invention still further provides a method of inhibiting cancer in a mammal. The method comprises administering to the mammal a cancer-inhibiting amount of a composition comprising an antibody produced in accordance with the method of claim 1, optionally in the form of a fusion protein, wherein the antibody or fusion protein thereof is optionally encoded in an isolated or purified nucleic acid molecule, which is optionally in the form of a vector and/or optionally contained within a cell, whereupon the cancer is inhibited in the mammal. The cancer can be lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, or pancreatic cancer.

EXAMPLES

The following examples serve to illustrate the present invention and are not intended to limit its scope in any way.

Example 1

Selection of Two Phage Fabs (m12 and m14) with High Affinity for Different Env-CD4 complexes by SAP We hypothesized that by sequential antigens during panning of phage display libraries and screening the enriched libraries using different antigens the selected phages will display Fabs against conserved epitopes shared among all antigens used during the entire selection process. Complexes of two different recombinant soluble Envs (gp140$_{89.6}$ and gp140$_{HXB2}$) with two-domain soluble CD4 (sCD4) were used as antigens for phage library panning as described in the Experimental Protocol. Screening of individual phage clones after panning was performed in phage ELISA with gp120 from 89.6, HXB2 and JR-FL, gp140 from 89.6 and JR-FL, and their complexes with sCD4. Interestingly, although the panning was performed using only two different antigens, significant number of phage clones exhibited significant binding to gp120 and sCD4-gp120 from another unrelated HIV isolate (JR-FL). Two phage clones, designated m12 and M14, were selected for further characterization based on their significant binding to all antigens used in the phage ELISA. In a control experiment to access the efficiency of the SAP methodology the panning was performed only with one antigen (sCD4-gp140$_{89.6}$). In this case none of the clones tested bound to sCD4-gp140$_{HXB2}$. Phagemid DNA of m12 and m14 was prepared and sequenced. The two clones exhibited significant differences in the amino acid composition and the length of their HCCDR3s.

Binding of Soluble Fab m12 and Fab m14 to gp120 from Different Isolates.

m12 bound gp120 from the primary isolates 89.6 and JR-FL with high affinity (nM), which significantly increased after binding of sCD4 to gp120, as measured by an ELISA assay. The affinity of m14 binding to gp120 from 89.6, JR-FL and HXB2 was not significantly increased after addition of sCD4 (Table 1).

Competition of m12 and m14 with Known Antibodies for gp120.

To further characterize the epitopes of m12 and m14 we measured their competition with anti-gp120 mAbs in the presence or absence of sCD4. m12 competed significantly with X5 Fab for binding to sCD4-gp120$_{JR-FL}$ complex, but much less for binding to gp120$_{JR-FL}$ alone. In contrast, m14 did not compete with X5 for binding to sCD4-gp120$_{JR-FL}$ complex but significantly competed for binding to gp120$_{JR-FL}$ alone. These differences are likely related to differences in the affinities of X5, m12 and m14 for gp120$_{JR-FL}$ and sCD4-gp120$_{JR-FL}$. IgG 17b did not compete with m12 and m14 for binding to gp120$_{JR-FL}$; IgG b12 competed with m12 and m14, although not very significantly. The competition pattern was not significantly dependent on the Env used at least for the Envs from the two isolates investigated in detail (89.6 and JR-FL). These results suggest that the epitopes of m12 and m14 are likely located in close proximity and partially overlap the X5 epitope.

Inhibition of Env-Mediated Membrane Fusion.

To determine the breadth and potency of HIV-1 neutralization by these Fabs we measured their ability to inhibit cell-cell fusion mediated by Envs of primary isolates from different clades in comparison with the potent broadly HIV neutralizing Fab X5 (Table 2). m14 inhibited cell-cell fusion mediated by Envs of primary isolates from different clades with a potency comparable (4 isolates), worse (1 isolate) or better (6 isolates) than X5 as measured by a cell fusion assay. These results suggest that m14 is a potent broadly HIV-1 neutralizing antibody. Due to technical difficulties in the production of m12 in sufficient amount, its potency was determined only for a few isolates and is comparable to that of X5.

Experimental Protocol

Cells, Viruses, Plasmids, Soluble CD4 (sCD4), gp120, gp140 and Antibodies.

293 cells were purchased from ATCC. The CEM cells expressing CCR5 (CEM-CCR5) were a gift from J. Moore (Cornell University, New York, N.Y.). All HIV isolates were obtained from the NIH AIDS Research and Reference Reagent Program (ARRRP). Recombinant vaccinia viruses used for the reporter gene fusion assay were described previously.[17] Plasmids used for expression of various Envs were obtained through the ARRRP from B. Hahn (University of Alabama at Birmingham). Two-domain soluble CD4 (sCD4) was obtained from the ARRRP. Purified gp120$_{89.6}$, gp140$_{89.6}$ and gp140$_{HXB2}$ were produced by recombinant vaccinia virus (gift of R. Doms, University of Pennsylvania, Philadelphia, Pa.) with a combination of lentil lectin affinity chromatography and size exclusion chromatography. Recombinant gp120$_{JR-FL}$ was a gift from A. Schultz and N. Miller (NIAID, Bethesda, Md.). Recombinant gp120$_{HXB2}$ was a gift from C. C. Broder (Uniformed Services University of the Health Sciences, Bethesda, Md.). The human monoclonal antibody X5 was produced as described[6], and the following antibodies were purchased: polyclonal sheep anti-gp120 antibody D7324 (Sigma), HRP conjugated monoclonal mouse anti-M13 antibody (Pharmacia, Uppsala, Sweden) and HRP conjugated polyclonal anti-human Fab antibodies (Jackson ImmunoResearch, Westgrove, Pa.).

Library Construction.

pComb3H library was constructed using pComb3H phagemid vector and 30 cc of bone marrow obtained from three long-term nonprogressors, whose sera had the broadest and most potent HIV-1 neutralization out of 37 candidates, and provided by Thomas Evans (University of Rochester).

Sequential Antigen Panning (SAP) of the Library and Analysis of Selected Phage Clones.

Phage ($5 \times 10^{12}$ cfu/ml) were preadsorbed on streptavidin-M280-Dynabeads in PBS for 1 h at room temperature (RT) followed by depletion in an immunotube (Nunc, Denmark) coated with 10 µg/ml sCD4 for 1 h at 37° C. Depleted phage library was incubated with 50 nM biotinylated HIV-1 envelope glycoprotein gp140$_{89.6}$ complexed with sCD4 in solution (gp140$_{89.6}$: sCD4=1:1 on molar level) for 2 h at RT with gentle agitation. Phage binding to biotinylated Env were separated from the phage library using streptavidin-M280-Dynabeads and a magnetic separator (Dynal). The beads were washed 20 times with 1 ml of PBS containing 0.1% Tween-20 and another 20 times with 1 ml of PBS. Bound phage were eluted by incubation at RT for 10 min with 1 ml of 100 mM TEA followed by neutralization with 0.5 ml of 1M, pH 7.5, Tris-HCl. Eluted phage were rescued by infection of E. coli TG1 cells and phage library was prepared for the next round of panning. For the $2^{nd}$ round of panning, 10 nM (2 nM for the 3$^{rd}$ round) of biotinylated gp140$_{89.6}$ complexed with sCD4 (1:1 on molar level) were used as antigen. For the 4$^{th}$ round of panning, 2 nM of biotinylated HIV-1 envelope glycoprotein gp140$_{HXB2}$ complexed with sCD4 (1:1 on molar level) were used as antigen. After 4$^{th}$ round of panning, 20 individual clones were screened for binding to gp140$_{89.6}$, gp120$_{JRFL}$, gp140$_{HXB2}$ complexed with sCD4. Single colonies were inoculated into 1 ml of 2×YT medium containing 100 µg/ml ampicillin and 2% glucose in 12-ml falcon tubes. The tubes were incubated overnight at 37° C./250 rpm. 10 µl of overnight culture from each tube were inoculated into 1 ml of 2×YT medium containing 100 µg/ml ampicillin, 2% glucose and about 4×10$^9$ cfu/ml of M$_{13}$KO$_7$ in 12-ml falcon tubes. The phage tubes were incubated at 37° C./250 rpm for 2 h and centrifuged at 4,000 rpm for 10 min at RT. The supernatant was removed and the cells were suspended in 1 ml of 2×YT medium with 100 µg/ml ampicillin and 50 µg/ml kanamycin. The tubes were then incubated overnight at 30° C./250 rpm. After 16 h, the tubes were centrifuged at 4,000 rpm for 10 min at 4° C. The supernatant was used for phage ELISA.

Phage ELISA.

ELISA was performed by using 96-well Nunc-Immuno™ Maxisorp™ surface plates (Nalge Nunc International, Denmark), which were coated overnight at 4° C. with 100 µl of gp120/140 (1 µg/ml in sodium bicarbonate buffer, pH 8.3) or gp120/140-sCD4 complex (100 µg/ml gp120/140 in PBS were premixed with equal volume of 100 µg/ml sCD4). After incubation at RT for 30 min, the mixture was diluted to 1 µg/ml in PBS), blocked in 100 µl of 4% non-fat dry milk in PBS for 1 hour at 37° C. After 4 washes with 0.05% Tween20/PBS washing buffer (WB), wells were incubated with 100 µl of phage supernatant for 2 hour at 37° C. Bound phage were detected by using horseradish peroxidase (HRP) labeled anti-M13 monoclonal antibody (Pharmacia) with incubation for 1 h at 37° C. and revealed by adding ready-to-use ABTs substrate (Pharmacia). Color development was performed at RT for 15 min and monitored at 405 nm.

Preparation of Soluble Fab Fragments.

Phagemid DNA from the selected clones was prepared and digested with Sac I and Spe I. The fragment bands were extracted and purified from agarose gel and ligated with phagemid pComb3X digested with the same enzymes. Ligated products were transformed to E. coli Top 10. pComb3X phagemid vector has amber stop codon between Fab insert and gIII, which allows expression of soluble Fab in a non-suppressor bacteria strain, like Top 10. Soluble Fabs were produced as described.[18] Protein G columns were used for purification.

Binding of Soluble Fabs.

ELISA was performed by using 96-well Nunc-Immuno™ Maxisorp™ surface plates. Coating of antigen and washing and blocking steps were the same as described in phage ELISA. Microplate wells were incubated with 100 µl two-fold serially diluted soluble Fab for 2 hour at 37° C. After 4 washes with WB, 100 µl a 1:2,500 dilution of HRP-conjugated goat anti-human IgG F(ab')$_2$ were added and incubated for 1 hour at 37° C. Following 4 washes with WB, the assay was developed at 37° C. for 15-30 minutes with ready-to-use ABTs substrate and monitored at 405 nm.

For competition ELISA, 50 µl of two-fold serially diluted competing mAbs were added to the blocked and washed wells, immediately followed by addition of 50 µl of biotinylated mAb (Bio-mAbs) previously determined to result in an ELISA signal that was 50 to 75% of maximum without competitor. After incubation for 2 h at 37° C., the wells were washed as above, probed with a streptavidin-HRP conjugate (Pierce) diluted 1:2,500 in PBS containing 2% non-fat dry milk and detected as above.

Cell-Cell Fusion Assay.

Cells (10$^5$ 293 cells), transfected with plasmids encoding various Envs under the control of the T7 promoter and infected with recombinant vaccinia virus encoding the T7 polymerase gene, were preincubated with m14 or X5 at 50 µg/ml for 30 min at 37° C., and then mixed with 10$^5$ CEM-CCR5 cells. The extent of cell fusion was quantified by counting the number of syncytia 12 h later. The data are presented in Table 2 as averages of duplicate samples and presented as % of fusion inhibition.

TABLE 1

Affinities of m12 and m14 to gp120 and sCD4-gp120.
Gp120 and gp120-sCD4 complexes were coated directly on 96-well plates, washed and m12 or m14 added at different concentrations. Bound Fabs were detected by anti-human F(ab')$_2$-HRP and measured as optical densities at 405 nm. The background was estimated by the amount of Fabs bound to BSA and subtracted. The data were fitted to the Langmuir adsorption isotherm: $B/B_{max} = F/(K_d + F)$, where B is the amount of bound Fab, $B_{max}$ is the maximal amount of bound Fab, F is its bulk concentration and $K_d$ is the equilibrium dissociation constant. The values of $K_d$ (nM) in parentheses are for the sCD4-gp120 complexes.

| Ab/Env | gp120$_{89.6}$ (+sCD4) | gp120$_{JR-FL}$ (+sCD4) | gp120$_{HXB2}$ (+sCD4) |
|---|---|---|---|
| m12 | 10(1) | 29(0.4) | nd |
| m14 | 5.4(7.3) | 0.9(1.2) | 0.3(0.4) |

TABLE 2

Inhibition of cell fusion mediated by Envs from various clades by m14 and X5.

| Env | UG0 37.8 | RW0 20.5 | US7 15.6 | HT5 93.1 | US0 05.11 | 89.6 | NL 4-3 | BR0 25.9 | TH0 22.4 | BR0 29.2 | UG9 75.10 |
|---|---|---|---|---|---|---|---|---|---|---|---|
| Clade | A | A | B | B | B | B | B | C | EA | F | G |
| m14 | 100 | 31 | 35 | 78 | 95 | 100 | 96 | 71 | 100 | 71 | 22 |
| X5 | 34 | 45 | 28 | 27 | 72 | 93 | 83 | 71 | 43 | 36 | 19 |

Example 2

Selection of Two Phage Fabs (M16 and M18) with High Affinity for Different Envs and Env-CD4 Complexes by SAP We hypothesized that by sequential antigens during panning of phage display libraries and screening the enriched libraries using different antigens, the selected phages will display Fabs against conserved epitopes shared among all antigens used during the entire selection process. Complexes of two different recombinant soluble Envs (gp140$_{89.6}$ and gp140$_{IIIB}$) with two-domain soluble CD4 (sCD4) and the Envs alone were used as antigens for phage library panning as described in the Experimental Protocol. After four rounds of panning each using different antigen, screening of individual phage clones was performed in phage ELISA with gp140$_{89.6}$, gp120$_{JR-FL}$ and gp140$_{IIIB}$, and their complexes with sCD4. Three clones were selected based on their binding to all six antigens used for screening including sCD4-gp120 and gp120 from an HIV isolate (JR-FL) which was not used for panning and has significant sequence differences compared to 89.6 and IIIB. Two of the clones were identical; thus two phage clones, designated m16 and m18, were selected for further characterization. Phagemid DNA of m16 and m18 was prepared and sequenced. The two clones exhibited significant differences in the amino acid composition and the length of their HCCDR3s. In a control experiment to access the efficiency of the SAP methodology the panning was performed only with one antigen (sCD4-gp140$_{89.6}$). In this case none of the clones tested bound to gp140$_{IIIB}$ or sCD4-gp140$_{IIIB}$.

Binding of Soluble Fab m16 and Fab m18 to gp120 and gp140 from Different Isolates.

m18 and m16 bound gp120 from the primary isolates 89.6 and JR-FL with an affinity (equilibrium dissociation constant) in the range from 0.1 to 1, and 1 to 10 nM, respectively, which was not significantly affected by sCD4 binding to gp120 as measured by an ELISA assay (Table 3). These results suggest that m16 and m18 are not CD4-inducible antibodies and that their epitopes are outside the CD4 binding site.

Competition of m16 and m18 with Known Antibodies for Binding to gp120.

To further characterize the epitopes of m16 and m18 we measured their competition with anti-gp120 mAbs for binding to gp120. The two antibodies showed almost identical patterns in their competition with X5, b12 and 17b. The competed significantly with b12 and to lesser extent with X5, and 17b (FIG. 4). The competition pattern was not significantly dependent of the Env used at least for the Envs from the two isolates investigated in detail (89.6 and JR-FL). These results suggest that the epitopes of m16 and m18 are likely located in close proximity to the coreceptor and CD4 binding sites where the X5, b12 and 17b epitopes are located.

Inhibition of Env-Mediated Membrane Fusion by m16 and m18.

To determine the breadth and potency of HIV-1 neutralization by m16 and m18 we measured their ability to inhibit cell-cell fusion mediated by Envs of primary isolates from different clades in comparison with the potent broadly HIV neutralizing Fab X5 (Table 4). For almost all isolates tested the two Fabs exhibited higher inhibitory activity than X5. These results suggest that m16 and m18 are potent broadly HIV-1 neutralizing antibodies.

Experimental Protocol

Cells, Viruses, Plasmids, Soluble CD4 (sCD4), gp120, gp140 and Antibodies.

Cells (293 cells) were purchased from ATCC. The CEM cells expressing CCR5 (CEM-CCR5) were a gift from J. Moore (Cornell University, New York, N.Y.). All HIV isolates were obtained from the NIH AIDS Research and Reference Reagent Program (ARRRP). Recombinant vaccinia viruses used for the fusion assay were described previously[17]. Plasmids used for expression of various Envs were obtained through the ARRRP from B. Hahn (University of Alabama at Birmingham). Two-domain soluble CD4 (sCD4) was obtained from the ARRRP. Purified gp120$_{89.6}$, gp140$_{89.6}$ and gp140$_{IIIB}$ were produced by recombinant vaccinia virus (gift of R Doms, University of Pennsylvania, Philadelphia, Pa.) with a combination of lentil lectin affinity chromatography and size exclusion chromatography. Recombinant gp120$_{JR-FL}$ was a gift from A. Schultz and N. Miller (NIAID, Bethesda, Md.). Recombinant gp120$_{IIIB}$ was a gift from C. Broder (Uniformed Services University of the Health Sciences, Bethesda, Md.). The human monoclonal antibody X5 was produced as described[6], and the following antibodies were purchased: polyclonal sheep anti-gp120 antibody D7324 (Sigma), HRP-conjugated monoclonal mouse anti-M13 antibody (Pharmacia, Uppsala, Sweden) and HRP-conjugated polyclonal anti-human Fab antibodies (Jackson ImmunoResearch, Westgrove, Pa.). The human monoclonal antibodies b12 and 17b were gifts from D. Burton (The Scripps Research Institute, La Jolla, Calif.) and J. Robinson (Tulane University Medical Center, New Orleans, La.), respectively.

Library Construction.

pComb3H library was constructed using pComb3H phagemid vector and 30 cc of bone marrow obtained from three long term nonprogressors whose sera had the broadest and most potent HIV-1 neutralization out of 37 candidates, and provided by Thomas Evans (University of Rochester).

Sequential Antigen Panning (SAP) of the Library and Analysis of Selected Phage Clones.

Phage (5×10$^{12}$ cfu/ml) were preadsorbed on streptavidin-M280-Dynabeads in PBS for 1 h at room temperature (RT) followed by depletion in an immunotube (Nunc, Denmark) coated with 10 µg/ml sCD4 for 1 h at 37° C. Depleted phage library was incubated with 50 nM biotinylated HIV-1 envelope glycoprotein gp140$_{89.6}$ complexed with sCD4 in solution (gp140$_{89.6}$: sCD4=1:1 on molar level) for 2 h at RT with gentle agitation. Phage binding to biotinylated envelope glycoprotein were separated from the phage library using streptavidin-M280-Dynabeads and a magnetic separator (Dynal). The beads were washed 20 times with 1 ml of PBS containing 0.1% Tween-20 and another 20 times with 1 ml of PBS. Bound phage were eluted by incubation at RT for 10 min with 1 ml of 100 mM TEA followed by neutralization with 0.5 ml of 1M, pH 7.5 Tris-HCl. Eluted phage were rescued by infection of *E. coli* TG1 cells and phage library was prepared for the next round of panning. For the 2$^{nd}$ round of panning, the phage library was preadsorbed on streptavidin-M280-Dynabeads and immobilized sCD4 as before and 50 nM of biotinylated gp140$_{IIIB}$ complexed with sCD4 (1:1 on molar level) used as antigen. For the 3$^{rd}$ and 4$^{th}$ rounds of panning, 10 nM (2 nM for 5$^{th}$ and 6$^{th}$ rounds) of biotinylated gp140$_{89.6}$ and gp140$_{IIIB}$ alone were sequentially used as antigens. For each library, 20 individual clones after the 4$^{th}$, 5$^{th}$ and 6$^{th}$ round of panning were screened by phage ELISA for binding to gp140$_{89.6}$, gp120$_{JRFL}$ and gp140$_{IIIB}$, and their complexes with sCD4 as follows. Single colonies were inoculated into 1 ml of 2×YT medium containing 100 µg/ml ampicillin and 2% glucose in 12-ml falcon tubes. The tubes were incubated overnight at 37° C./250 rpm. 10 µl of overnight culture from each tube were inoculated into 1 ml of 2×YT medium containing 100 µg/ml ampicillin, 2% glucose and about 4×10$^9$ cfU/ml of M$_{13}$KO$_7$ in 12-ml falcon tubes. The phage tubes were incubated at 37° C./250 rpm for 2 h and centrifuged at 4,000 rpm for 10 min at RT. The supernatant was removed and the cells were suspended in 1 ml of 2×YT medium with 100 µg/ml ampicillin and 50 µg/ml kanamycin. The tubes were then incubated overnight at 30° C./250 rpm. After 16 h, the tubes were centrifuged at 4,000 rpm for 10 min at 4° C. The supernatant was used for phage ELISA.

Phage ELISA.

ELISA was performed by using 96-well Nunc-Immuno™ Maxisorp™ surface plates (Nalge Nunc International, Denmark) which were coated overnight at 4° C. with 100 µl of gp120/140 (1 µg/ml in sodium bicarbonate buffer, pH 8.3) or gp120/140-sCD4 complex (100 µg/ml gp120/140 in PBS were premixed with equal volume of 100 µg/ml sCD4. After incubation at RT for 30 min, the mixture was diluted to 1 µg/ml in PBS), blocked in 100 µl of 4% non-fat dry milk in PBS for 1 hour at 37° C. After 4 washes with 0.05% Tween20/PBS washing buffer (WB), wells were incubated with 100 µl of phage supernatant for 2 hour at 37° C. Bound phage were detected by using horse radish peroxidase (HRP) labeled anti-M13 monoclonal antibody (Pharmacia) with incubation for 1 h at 37° C. and revealed by adding ready-to-use ABTs substrate (Pharmacia). Color development was performed at RT for 15 min and monitored at 405 nm.

Preparation of Soluble Fab Fragments.

Phagemid DNA from the selected clones was prepared and digested with Sac I and Spe I. The fragment bands were extracted and purified from agarose gel and ligated with phagemid pComb3X digested with the same enzymes. Ligated products were transformed to *E coli* Top 10. pComb3X phagemid vector has amber stop codon between Fab insert and gIII, which allows expression of soluble Fab in a non-suppressor bacteria strain, like Top 10. Soluble Fabs were produced as described. [18]Protein G columns were used for purification.

Binding of Soluble Fabs.

ELISA was performed by using 96-well Nunc-Immuno™ Maxisorp™ surface plates. Coating of antigen and washing and blocking steps were the same as described in phage ELISA. Microplate wells were incubated with 100 µl two-fold serially diluted soluble Fab for 2 hour at 37° C. After 4 washes with WB, 100 µl of a 1:2,500 dilution of HRP-conjugated goat anti-human IgG F(ab')$_2$ was added and incubated for 1 hour at 37° C. Following 4 washes with WB, the assay was developed at 37° C. for 15-30 minutes with ready-to-use ABTs substrate and monitored at 405 nm. For competition ELISA, 50 µl of two-fold serially diluted competing mAbs were added to the blocked and washed wells, immediately followed by addition of 50 µl of biotinylated mAb (Bio-mAbs) previously determined to result in an ELISA signal that was 50 to 75% of maximum without competitor. After incubation for 2 h at 37° C., the wells were washed as above, probed with a streptavidin-HRP conjugate (Pierce) diluted 1:2,500 in PBS containing 2% non-fat dry milk and detected as above. For capture ELISA, 1 µg/ml polyclonal sheep anti-gp120 antibody D7324 was coated on the microplate to capture Envs. Then the Env was added and the steps described above were followed.

Cell-Cell Fusion Assay.

Cells ($10^5$ 293 cells), transfected with plasmids encoding various Envs under the control of the T7 promoter and infected with recombinant vaccinia virus encoding the T7 polymerase gene, were preincubated with M14 or X5 at 50 µg/ml for 30 min at 37° C., and then mixed with $10^5$ CEM-CCR5 cells. The extent of cell fusion was quantified by counting the number of syncytia 12 h later.

TABLE 3

Affinity of m18 to gp120 and sCD4-gp120. Gp120 and gp120-sCD4 complexes were coated directly on 96-well plates, washed and m18 added at different concentrations. Bound Fabs were detected by anti-human F(ab')$_2$-HRP and measured as optical densities at 405 nm. The background was estimated by the amount of Fabs bound to BSA and subtracted. The data were fitted to the Langmuir adsorption isotherm: $B/B_{max} = F/(K_d + F)$, where B is the amount of bound Fab, $B_{max}$ is the maximal amount of bound Fab, F is its bulk concentration and $K_d$ is the equilibrium dissociation constant. The values of $K_d$ (nM) in parentheses are for the sCD4-gp120 complexes.

| Ab/Env | gp120$_{89.6}$ (+sCD4) | gp120$_{JR-FL}$ (+sCD4) | gp120$_{IIIB}$ (+sCD4) |
|---|---|---|---|
| m18 | 1.0(0.9) | 0.9(0.7) | 0.08(0.09) |

TABLE 4

Inhibition of cell fusion mediated by Envs from various clades by m18 and X5. Cells ($10^5$ 293 cells), transfected with plasmids encoding various Envs under the control of the T7 promoter and infected with recombinant vaccinia virus encoding the T7 polymerase gene, were preincubated with m18 or X5 at 50 µg/ml for 30 min at 37° C., and then mixed with $10^5$ CEM-CCR5 cells. The extent of cell fusion was quantified by counting the number of syncytia 12 h later. The data are averages of duplicate samples and presented as % of fusion inhibition.

| Env | UG0 37.8 | RW0 20.5 | US7 15.6 | HT5 93.1 | US0 05.11 | 89.6 | NL 4-3 | BR0 25.9 | TH0 22.4 | BR0 29.2 | UG9 75.10 |
|---|---|---|---|---|---|---|---|---|---|---|---|
| Clade | A | A | B | B | B | B | B | C | EA | F | G |
| m16 | 34 | 67 | 63 | 44 | 94 | 100 | 67 | 86 | 100 | 86 | 52 |
| m18 | 34 | 25 | 97 | 39 | 93 | 100 | 92 | 86 | 93 | 86 | 56 |
| X5 | 34 | 45 | 28 | 27 | 72 | 93 | 83 | 71 | 43 | 36 | 19 | probed with a streptavidin-HRP conjugate (Pierce) diluted 1:2,500 in PBS containing 2% non-fat dry milk and detected as above. For capture ELISA, 1 µg/ml polyclonal sheep anti-gp120 antibody D7324 was coated on the microplate to capture Envs. Then the Env was added and the steps described above were followed. The data are presented in Table 5.

TABLE 5

Binding of m18 to gp140 from primary isolates.

| Envelope gp140 | EC50, nM | SD |
|---|---|---|
| UG037.8 | 0.83 | 0.014 |
| HT593.1 | 0.25 | 0.01 |
| MW965.26 | 0.55 | 0.022 |
| BR019.10 | 0.77 | 0.11 |
| UG024.2 | 0.97 | 0.044 |
| ZR001.3 | 1.07 | 0.013 |
| UG975-10 | 0.87 | 0.034 |
| Bal-L | 0.53 | 0.002 |
| R2 | 0.13 | 0.007 |
| 89.6 | 1.17 | 0.007 |
| CM243 | 116.13 | 1.43 |
| IIIB* | 0.48 | 0.002 |

*gp120

In this assay format single-round infectious molecular clones, produced by envelope complementation, was used. The degree of virus neutralization by antibody was achieved by measuring luciferase activity. Briefly, $2 \times 10^4$ U87.CD4.CCR5.CXCR4 cells in 100 µl of medium (DMEM containing 15% FBS, 1 µg of puromycin/ml, 300 µg of G418/ml, glutamine, and penicillin-streptomycin) were added to microplate wells (96-well flat-bottom; Corning Inc., Corning, N.Y.) and incubated for 24 h at 37° C. in 5% $CO_2$. One hundred microliters of medium containing an amount of virus previously determined to yield ~100,000 counts were mixed with various amounts of antibody, incubated for 1 h at 37° C., added to the cells, and incubated for a further 3 days. The wells were aspirated and washed once with PBS, and 60 µl of luciferase cell culture lysis reagent (Promega, Madison, Wis.) were added. The wells were scraped and the lysate was mixed by pipetting, 50 µl were transferred to a round-bottom plate (Corning), and the plate was centrifuged at 1,800×g for 10 min at 4° C. Twenty microliters were transferred to an opaque assay plate (Corning), and the luciferase activity was measured on a luminometer (EG&G Berthold LB 96V; Perkin Elmer, Gaithersburg, Md.) by using luciferase assay reagent (Promega).

TABLE 6 m14 and m18 neutralization activity in Luciferase assay

| | m14 | | m18 | |
|---|---|---|---|---|
| Virus | IC50 | IC90 | IC50 | IC90 |
| HxB2 | 1 | 7 | 0.1 | 7 |
| 89.6 | 8 | 25 | 10 | >20 |
| JRCSF | 5 | 50 | >200 | >200 |
| YU2 | 7 | 33 | >200 | >200 |

Pseudotype viruses were prepared by cotransfection of 70% to 80%-confluent 293T cells with pNL4-3.luc.E-R- (NIH ARRRP) and pSV7d-env plasmid using the calcium phosphate/HEPES buffer technique, according to manufacturers instruction (Promega). Sixteen hours after the transfection the media was removed and replaced with media supplemented with 0.1 mM sodium butyrate (Sigma). Cells were allowed to grow for an additional 24 hrs. The supernatant was harvested, centrifuged at 16,000 rpm for 5 min at 4° C., filtered through a 0.45 µm pore filter and either used fresh or kept frozen at −80° C. Neutralization assays were carried out using HOS $CD4^+$ $CCR5^+$, or HOS $CD4^+$ $CXCR4^+$ cells, as appropriate. Infectivity titers were determined on the basis of luminescence measurements at 3 days post infection of the cells by the pseudotyped viruses. Neutralization assays were carried out in triplicate wells by preincubation of serial dilutions of Fab monoclonal antibodies (Mab) with pseudotype viruses for 1 hr at 4° C. followed by infection of $1-2 \times 10^4$ HOS $CD4^+$ $CCR5^+$ cells. Luminesence was measured after 3 days. The mean luminescence readings for triplicate wells were determined, and the endpoint was considered to be the last dilution of Mab at which the mean results from the test samples were less than 50% of the nonneutralized control mean. Neutralization assays for each envelope clone against the Fab Mabs were carried out at least three times. The data are presented in Table 7.

TABLE 7

M14 and M18 neutralization activity in pseudovirus assay

| HIV-1 Group | HIV-1 isolates | M14 Concentration (µg/ml) of Fab | M18 Concentration (µg/ml) of Fab |
|---|---|---|---|
| Clade A | 92RW020.5 | nd | 3 |
| Clade B | R2 | 2.24 | 1.6 |
| | V5 | nd | <2 |
| | P37 | nd | 100 |
| | #6-4/41 | >100 | 100 |
| | #8-4/49 | 35.4 | 5 |
| | #4-4/116 | >100 | 6.3 |
| | #9-131 | 100 | >100 |
| | VI1399 | >100 | >100 |
| | VI1273 | 3.1 | 25 |
| | MN-TCLA | 2.24 | <1.6 |
| Clade C | GX-C44 | 8.8 | >25 |
| Clade D | Z2Z6 | 50 | 25 |
| Clade E | GX-E14 | 100 | >100 |
| | TH966 | >100 | >100 |
| Clade F | VI14004[b] | nd | <2 |

Throughout this application, various publications are referenced. The disclosures of these publications in their entireties are hereby incorporated by reference into this application in order to more fully describe the state of the art to which this invention pertains. The references disclosed are also individually and specifically incorporated by reference herein for the material contained in them that is discussed in the sentence in which the reference is relied upon. If the number designation is not associated with a particular number it will be clear to one of skill which reference is being referred to by the context the reference is relied upon and by a review of the various possible references. The examples all refer to a particular set of references, and thus do not have a letter designation associated with individual numbers.

It will be apparent to those skilled in the art that various modifications and variations can be made in the present invention without departing from the scope or spirit of the invention. It will also be apparent to those skilled in the art that nucleic acid sequences are disclosed by the disclosure of the amino acid sequences as one skilled in the art will know what nucleic acids comprise an amino acid. Other embodiments of the invention will be apparent to those skilled in the art from consideration of the specification and practice of the invention disclosed herein. It is intended that the specification

REFERENCES

1. Dimitrov, Cell biology of virus entry. *Cell* 101, 697-702 (2000).
2. Chan et al., HIV entry and its inhibition. *Cell* 93, 681-684 (1998).
3. Sodroski, HIV-1 entry inhibitors in the side pocket. *Cell* 99, 243-246 (1999).
4. Dimitrov, Fusin—a place for HIV-1 and T4 cells to meet. Identifying the coreceptor mediating HIV-1 entry raises new hopes in the treatment of AIDS. *Nature Medicine* 2, 640-641 (1996).
5. LaCasse et al., Fusion-competent vaccines: broad neutralization of primary isolates of HIV. *Science* 283, 357-362 (1999).
6. Moulard et al., Broadly cross-reactive HIV-1 neutralizing human monoclonal antibody selected for binding to gp120-CD4-CCR5 complexes. *PNAS USA* 99 (10): 6913-6918 (2002).
7. Burton et al., Efficient neutralization of primary isolates of HIV-1 by a recombinant human monoclonal antibody. *Science* 266, 1024-1027 (1994).
8. Muster et al., A conserved neutralizing epitope on gp41 of human immunodeficiency virus type 1. *J. Virol.* 67, 6642-6647 (1993).
9. Conley et al., Neutralization of divergent human immunodeficiency virus type 1 variants and primary isolates by IAM-41-2F5, an anti-gp41 human monoclonal antibody. *Proc. Natl. Acad. Sci. U.S.A.* 91, 3348-3352 (1994).
10. Trkola et al., Human monoclonal antibody 2G12 defines a distinctive neutralization epitope on the gp120 glycoprotein of human immunodeficiency virus type 1. *J. Virol.* 70, 1100-1108 (1996).
11. Zwick et al., Broadly Neutralizing Antibodies Targeted to the Membrane-Proximal External Region of Human Immunodeficiency Virus Type 1 Glycoprotein gp41. *J. Virol.* 75, 10892-10905 (2001).
12. Celada et al., Antibody raised against soluble CD4-rgp120 complex recognizes the CD4 moiety and blocks membrane fusion without inhibiting CD4-gp120 binding. *J. Exp. Med.* 172, 1143-1150 (1990).
13. Gershoni et al., HIV binding to its receptor creates specific epitopes for the CD4/gp120 complex. *FASEB J.* 7, 1185-7. (1993).
14. Kang et al., Immunization with a soluble CD4-gp120 complex preferentially induces neutralizing anti-human immunodeficiency virus type 1 antibodies directed to conformation-dependent epitopes of gp120. *J. Virol.* 68, 5854-5862 (1994).
15. Devico et al., Covalently crosslinked complexes of human immunodeficiency virus type 1 (HIV-1) gp120 and CD4 receptor elicit a neutralizing immune response that includes antibodies selective for primary virus isolates. *Virology* 218, 258-263 (1996).
16. Sullivan et al., CD4-Induced conformational changes in the human immunodeficiency virus type 1 gp120 glycoprotein: consequences for virus entry and neutralization. *J. Virol.* 72, 4694-4703 (1998).
17. Nussbaum et al., Fusogenic mechanisms of enveloped-virus glycoproteins analyzed by a novel recombinant vaccinia virus-based assay quantitating cell fusion-dependent reporter gene activation. *J. Virol.* 68, 5411-5422 (1994).
18. Barbas et al., G.J. Phage Display: A Laboratory Mannual. Cold Spring Harbor Laboratory Press, Cold Spring Harbor (2001).

What is claimed is:

1. An isolated antibody or antibody fragment to HIV envelope glycoprotein that can recognize one or more strains of HIV, wherein the antibody or antibody fragment comprises the sequence of SEQ ID NO: 1 or a variant thereof, wherein the variant comprises the sequence of SEQ ID NO: 13 as complementarity determining region 3 (CDR3), and retains the ability to bind to the same epitope on HIV envelope glycoprotein as that of the sequence of SEQ ID NO: 1.

2. The antibody or antibody fragment of claim 1, wherein the antibody or antibody fragment is a scFv.

3. The antibody or antibody fragment of claim 1, wherein the antibody or antibody fragment is a Fab.

4. The isolated antibody or antibody fragment of claim 1, wherein the variant of SEQ ID NO: 1 further comprises the sequence of SEQ ID NO: 12 as complementarity determining region 2 (CDR2).

5. The antibody or antibody fragment of claim 4, wherein the variant of SEQ ID NO: 1 further comprises the sequence of SEQ ID NO: 11 as complementarity determining region 1 (CDR1).

6. The antibody or antibody fragment of claim 1, wherein the antibody or antibody fragment further comprises the sequence of SEQ ID NO: 6 or a variant thereof comprising the sequence of SEQ ID NO: 16 as CDR3.

7. The antibody or antibody fragment of claim 6, wherein the variant of SEQ ID NO: 6 further comprises the sequence of SEQ ID NO: 15 as complementarity determining region 2 (CDR2).

8. The antibody or antibody fragment of claim 7, wherein the variant of SEQ ID NO: 6 further comprises the sequence of SEQ ID NO: 14 as complementarity determining region 1 (CDR1).

9. The antibody or antibody fragment of claim 6, wherein the variant of SEQ ID NO: 1 further comprises the sequence of SEQ ID NO: 12 as the CDR2.

10. The antibody or antibody fragment of claim 9, wherein the variant of SEQ ID NO: 1 further comprises the sequence of SEQ ID NO: 11 as the CDR1.

11. The antibody or antibody fragment of claim 10, wherein the variant of SEQ ID NO: 6 further comprises the sequence of SEQ ID NO: 15 as the CDR2.

12. The antibody or antibody fragment of claim 11, wherein the variant of SEQ ID NO: 6 further comprises the sequence of SEQ ID NO: 14 as the CDR1.

13. The antibody or antibody fragment of claim 6, wherein the variant of SEQ ID NO: 1 further comprises the sequence of SEQ ID NO: 12 as the CDR2, and the variant of SEQ ID NO: 6 further comprises the sequence of SEQ ID NO: 15 as the CDR2.

14. The antibody or antibody fragment of claim 13, wherein the variant of SEQ ID NO: 6 further comprises the sequence of SEQ ID NO: 14 as the CDR1.

15. An isolated antibody or antibody fragment to HIV envelope glycoprotein that can recognize one or more strains of HIV, wherein the antibody or antibody fragment comprises the sequence of SEQ ID NO: 1, the sequence of SEQ ID NO: 6, or both the sequence of SEQ ID NO: 1 and the sequence of SEQ ID NO: 6.

16. The antibody or antibody fragment of claim 15, wherein the antibody or antibody fragment comprises the sequence of SEQ ID NO: 1.

17. The antibody or antibody fragment of claim 15, wherein the antibody or antibody fragment comprises the sequence of SEQ ID NO: 6.

18. The antibody or antibody fragment of claim 15, wherein the antibody or antibody fragment comprises both the sequence of SEQ ID NO: 1 and the sequence of SEQ ID NO: 6.

19. The antibody or antibody fragment of claim 15, wherein the antibody or antibody fragment is a scFv.

20. The antibody or antibody fragment of claim 15, wherein the antibody or antibody fragment is a Fab.

* * * * *

SEQUENCE LISTING

```
<160> NUMBER OF SEQ ID NOS: 16

<210> SEQ ID NO 1
<211> LENGTH: 233
<212> TYPE: PRT
<213> ORGANISM: Artificial
<220> FEATURE:
<223> OTHER INFORMATION: Synthetic

<400> SEQUENCE: 1

Val Gln Leu Leu Glu Ser Gly Pro Gly Leu Val Lys Pro Ser Gln Thr
1               5                   10                  15

Leu Ser Leu Thr Cys Thr Val Ser Gly Gly Ser Ile Ser Thr Gly Asp
            20                  25                  30

Tyr Tyr Trp Ser Trp Ile Arg Gln Ser Pro Gly Lys Gly Leu Glu Trp
        35                  40                  45

Ile Gly Tyr Ile Ser Ser Ser Gly Asn Thr Tyr Tyr Asn Pro Ser Leu
    50                  55                  60

Thr Ser Arg Val Val Ile Ser Phe Asp Thr Ser Met Asn Gln Phe Ser
65                  70                  75                  80

Leu Lys Val Asp Ser Val Thr Ala Ala Asp Thr Ala Val Tyr Tyr Cys
                85                  90                  95

Ala Arg Glu Arg Arg Val Leu Leu Trp Leu Gly Phe Pro Arg Gly Gly
```

```
                100                 105                 110
Leu Asp Tyr Trp Gly Gln Gly Thr Leu Val Thr Val Ser Ser Ala Ser
            115                 120                 125

Thr Lys Gly Pro Ser Val Phe Pro Leu Ala Pro Ser Ser Lys Ser Thr
        130                 135                 140

Ser Gly Gly Thr Ala Ser Leu Asp Cys Leu Val Lys Asp Tyr Phe Pro
145                 150                 155                 160

Glu Pro Val Met Val Ser Trp Asn Ser Gly Ala Leu Thr Ser Gly Val
                165                 170                 175

His Thr Leu Ala Ala Val Ile Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn Arg Lys Pro Ser Asn Thr Lys Val Asp Asn Lys Val
        210                 215                 220

Glu Pro Lys Ser Cys Asp Lys Thr Ser
225                 230

<210> SEQ ID NO 2
<211> LENGTH: 228
<212> TYPE: PRT
<213> ORGANISM: Artificial
<220> FEATURE:
<223> OTHER INFORMATION: Synthetic

<400> SEQUENCE: 2

Val Gln Leu Leu Glu Ser Gly Pro Gly Val Val Lys Pro Ser Glu Thr
1               5                   10                  15

Leu Ser Leu Thr Cys Thr Val Ser Gly Ala Ser Val Asn Asn Tyr Tyr
            20                  25                  30

Trp Thr Trp Val Arg Gln Pro Pro Gly Lys Gly Leu Glu Trp Ile Gly
        35                  40                  45

Asn Val Tyr Asp Ser Gly Asp Thr Asn Tyr Asn Pro Ser Leu Ser Ser
    50                  55                  60

Arg Leu Ser Leu Ser Met Asp Thr Ser Lys Asn Gln Phe Ser Leu Arg
65                  70                  75                  80

Leu Ser Ser Val Thr Ala Ala Asp Thr Ala Thr Tyr Tyr Cys Ala Arg
                85                  90                  95

Tyr His Arg His Phe Ile Arg Gly Pro Leu Ser Phe Asp Tyr Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Tyr Lys Ser Thr Ser Gly Gly Thr Ser
    130                 135                 140

Ser Leu Asp Ser Leu Val Lys Asp Ser Phe Pro Glu Pro Val Met Val
145                 150                 155                 160

Ser Trp Asn Ser Gly Ala Leu Thr Arg Gly Val His Thr Phe Pro Ala
                165                 170                 175

Val Ile Gln Ser Ala Gly Leu Tyr Ser Leu Ile Ser Val Val Thr Val
            180                 185                 190

Pro Ser Ser Ser Met Gly Thr Gln Thr Tyr Ile Cys Asn Val Asn Arg
        195                 200                 205

Lys Pro Ser Asn Thr Lys Val Val Asn Lys Asp Glu Pro Lys Ser Cys
    210                 215                 220

Asp Lys Thr Ser
```

<210> SEQ ID NO 3
<211> LENGTH: 231
<212> TYPE: PRT
<213> ORGANISM: Artificial
<220> FEATURE:
<223> OTHER INFORMATION: Synthetic

<400> SEQUENCE: 3

Val Gln Leu Leu Glu Ser Gly Pro Gly Leu Val Lys Pro Ser Gln Ser
1               5                   10                  15

Leu Ser Leu Thr Cys Ala Ile Ser Gly Asp Ser Leu Ser Ser Asp Ser
            20                  25                  30

Thr Ala Trp Asn Trp Ile Arg Gln Ser Pro Ser Arg Gly Leu Glu Trp
        35                  40                  45

Leu Gly Arg Thr Tyr Tyr Arg Ser Thr Trp Phe Tyr Asp Tyr Ala Glu
    50                  55                  60

Ser Val Lys Ser Arg Ile Asn Ile Asn Pro Asp Thr Ser Lys Ser Gln
65                  70                  75                  80

Phe Ser Leu Gln Leu Arg Ser Val Thr Pro Glu Asp Thr Ala Val Tyr
                85                  90                  95

Tyr Cys Ala Arg Asp Phe Asn Lys Gly Ala Gly Tyr Asn Trp Phe Asp
            100                 105                 110

Pro Trp Gly Pro Gly Thr Val Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Asp Cys Leu Val Lys Asp Tyr Phe Pro Glu Pro
145                 150                 155                 160

Val Met Val Ser Trp Asn Ser Gly Ala Leu Thr Ser Gly Val His Thr
                165                 170                 175

Leu Ala Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn Arg Lys Pro Ser Asn Thr Lys Val Val Lys Lys Asp Glu Pro
    210                 215                 220

Lys Ser Cys Asp Lys Thr Ser
225                 230

<210> SEQ ID NO 4
<211> LENGTH: 237
<212> TYPE: PRT
<213> ORGANISM: Artificial
<220> FEATURE:
<223> OTHER INFORMATION: Synthetic

<400> SEQUENCE: 4

Val Gln Leu Leu Glu Ser Gly Ala Glu Val Lys Arg Pro Gly Ser Ser
1               5                   10                  15

Val Arg Val Ser Cys Gln Val Ser Gly Gly Ser Phe Ser Asn Tyr Ala
            20                  25                  30

Val Ser Trp Val Arg Gln Thr Pro Gly His Gly Leu Glu Trp Met Gly
        35                  40                  45

Gly Ile Ile Pro Met Phe Asn Ala Pro Asn Tyr Ala Gln Lys Phe His
    50                  55                  60

```
Gly Arg Val Thr Phe Ile Ala Asp Glu Ser Thr Arg Thr Val His Met
 65                  70                  75                  80

Glu Leu Arg Ser Leu Arg Ser Glu Asp Thr Ala Val Tyr Phe Cys Ala
                 85                  90                  95

Thr Ala Ser Glu Ala Thr Glu Asn Asp Tyr Tyr Gln Ser Pro Thr His
            100                 105                 110

Tyr Tyr Ala Met Asp Val Trp Gly Gln Gly Thr Ala Val Thr Val Phe
        115                 120                 125

Ser Ser Ala Ser Thr Lys Gly Pro Leu Val Phe Pro Leu Ala Pro Ser
130                 135                 140

Ser Lys Ser Ala Phe Gly Gly Thr Ala Ser Leu Asp Ser Leu Val Lys
145                 150                 155                 160

Asp Ser Leu Pro Glu Pro Val Met Val Ser Trp Asn Ser Gly Ala Leu
                165                 170                 175

Thr Thr Gly Val Arg Thr Leu Ala Ala Val Ile Gln Ser Ala Gly Leu
            180                 185                 190

Tyr Ser Leu Ile Ser Val Val Thr Val Pro Ser Ser Ser Leu Gly Thr
        195                 200                 205

Gln Thr Tyr Ile Cys Asn Val Asn Arg Lys Pro Ser Asn Ile Lys Val
    210                 215                 220

Val Asn Arg Asp Glu Pro Lys Ser Cys Val Lys Asn Ser
225                 230                 235

<210> SEQ ID NO 5
<211> LENGTH: 214
<212> TYPE: PRT
<213> ORGANISM: Artificial
<220> FEATURE:
<223> OTHER INFORMATION: Synthetic

<400> SEQUENCE: 5

Thr Leu Thr Gln Ser Pro Thr Thr Leu Ser Ala Ser Pro Gly Glu Arg
  1               5                  10                  15

Val Ile Leu Ser Cys Arg Ala Ser Gln Ser Val Ser Ser Ser His Leu
                 20                  25                  30

Ala Trp Tyr Gln Gln Arg Pro Gly Gln Thr Pro Arg Leu Leu Ile Tyr
             35                  40                  45

Ser Ser Ser Ser Arg Ala Ala Gly Ile Pro Asp Arg Phe Ser Gly Ser
 50                  55                  60

Gly Ser Gly Thr Asp Phe Thr Leu Thr Ile Ser Arg Leu Glu Pro Glu
 65                  70                  75                  80

Asp Phe Ala Val Tyr Tyr Cys Gln Asn Gln Gly Phe Ser Pro Arg Phe
                 85                  90                  95

Phe Phe Gly Pro Gly Thr Thr Val Asp Met Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Leu Leu Ser Ser Pro Val Thr Lys Ser
        195                 200                 205

Phe Asn Arg Gly Glu Cys
    210

<210> SEQ ID NO 6
<211> LENGTH: 210
<212> TYPE: PRT
<213> ORGANISM: Artificial
<220> FEATURE:
<223> OTHER INFORMATION: Synthetic

<400> SEQUENCE: 6

Thr Gln Ser Pro Gly Thr Leu Ser Leu Ser Pro Gly Glu Arg Ala Thr
1               5                   10                  15

Leu Ser Cys Arg Ala Ser His Ser Val Ser Arg Ala Tyr Leu Ala Trp
            20                  25                  30

Tyr Gln Gln Lys Pro Gly Gln Ala Pro Arg Leu Leu Ile Tyr Gly Thr
        35                  40                  45

Ser Ser Arg Ala Thr Gly Ile Pro Asp Arg Phe Ser Gly Ser Gly Ser
    50                  55                  60

Gly Thr Asp Phe Thr Leu Thr Ile Ser Arg Leu Glu Pro Glu Asp Phe
65                  70                  75                  80

Ala Val Tyr Tyr Cys Gln Gln Tyr Gly Gly Ser Pro Trp Phe Gly Gln
                85                  90                  95

Gly Thr Lys Val Glu Leu Lys Arg Thr Val Ala Ala Pro Ser Val Phe
            100                 105                 110

Ile Phe Pro Pro Ser Asp Glu Gln Leu Lys Ser Gly Thr Ala Ser Val
        115                 120                 125

Val Cys Leu Leu Asn Asn Phe Tyr Pro Arg Glu Ala Lys Val Gln Trp
    130                 135                 140

Lys Val Asp Asn Ala Leu Gln Ser Gly Asn Ser Gln Glu Ser Val Thr
145                 150                 155                 160

Glu Gln Asp Ser Lys Asp Ser Thr Tyr Ser Leu Ser Ser Thr Leu Thr
                165                 170                 175

Leu Ser Lys Ala Asp Tyr Glu Lys His Lys Val Tyr Ala Cys Glu Val
            180                 185                 190

Thr His Gln Leu Leu Ser Ser Pro Val Thr Lys Ser Phe Asn Arg Gly
        195                 200                 205

Glu Cys
    210

<210> SEQ ID NO 7
<211> LENGTH: 212
<212> TYPE: PRT
<213> ORGANISM: Artificial
<220> FEATURE:
<223> OTHER INFORMATION: Synthetic

<400> SEQUENCE: 7

Gln Met Thr Gln Ser Pro Ser Ser Val Ser Ala Ser Val Gly Asp Arg
1               5                   10                  15

Val Thr Ile Thr Cys Arg Ala Ser Gln Gly Ile Ser Ser Trp Leu Ala
            20                  25                  30

Trp Tyr Gln Gln Lys Pro Gly Lys Ala Pro Lys Leu Leu Ile Asn Ala
        35                  40                  45

Ala Ser Ser Leu Gln Ser Gly Val Pro Ser Arg Phe Ser Gly Ser Gly
    50                  55                  60
```

-continued

Ser Gly Thr Asp Phe Thr Leu Thr Ile Ser Ser Leu Gln Pro Glu Asp
65                  70                  75                  80

Phe Ala Thr Tyr Tyr Cys Gln Gln Ala Asn Ser Phe Pro Leu Thr Phe
                85                  90                  95

Gly Gly Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Leu Leu Ser Ser Pro Val Thr Lys Ser Phe Asn
        195                 200                 205

Arg Gly Glu Cys
    210

<210> SEQ ID NO 8
<211> LENGTH: 212
<212> TYPE: PRT
<213> ORGANISM: Artificial
<220> FEATURE:
<223> OTHER INFORMATION: Synthetic

<400> SEQUENCE: 8

Gln Met Thr Gln Ser Pro Ser Phe Leu Ser Ala Ser Val Gly Asp Arg
1               5                   10                  15

Val Ser Ile Thr Cys Arg Ala Ser Gln Asp Ile Gln Lys Phe Leu Ala
            20                  25                  30

Trp Tyr Gln Leu Thr Pro Gly Asp Ala Pro Lys Leu Leu Met Tyr Ser
        35                  40                  45

Ala Ser Thr Leu Gln Ser Gly Val Pro Ser Arg Phe Ser Gly Ser Gly
    50                  55                  60

Ser Gly Thr Glu Phe Thr Leu Thr Ile Ser Gly Leu Gln Pro Glu Asp
65                  70                  75                  80

Phe Ala Thr Tyr Tyr Cys Gln His Leu Lys Arg Tyr Pro Tyr Thr Phe
                85                  90                  95

Gly Gln Gly Thr Lys Leu Glu Ile Ser Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Asn Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Leu Leu Ser Ser Pro Val Thr Lys Ser Phe Asn
        195                 200                 205

Arg Gly Glu Cys
    210

<210> SEQ ID NO 9
<211> LENGTH: 609
<212> TYPE: DNA
<213> ORGANISM: Artificial
<220> FEATURE:
<223> OTHER INFORMATION: Synthetic

<400> SEQUENCE: 9

| | | | | | |
|---|---|---|---|---|---|
| atgaaccggg | gagtcccttt | taggcacttg | cttctggtgc | tgcaactggc | gctcctccca | 60 |
| gcagccactc | agggaaagaa | agtggtgctg | ggcaaaaaag | gggatacagt | ggaactgacc | 120 |
| tgtacagctt | cccagaagaa | gagcatacaa | ttccactgga | aaaactccaa | ccagataaag | 180 |
| attctgggaa | atcagggctc | cttcttaact | aaaggtccat | ccagctgaa | tgatcgcgct | 240 |
| gactcaagaa | gaagcctttg | ggaccaagga | aactttcccc | tgatcatcaa | gaatcttaag | 300 |
| atagaagact | cagatactta | catctgtgaa | gtggaggacc | agaaggagga | ggtgcaattg | 360 |
| ctagtgttcg | gattgactgc | caactctgac | acccacctgc | ttcaggggca | gagcctgacc | 420 |
| ctgaccttgg | agagccccc | tggtagtagc | ccctcagtgc | aatgtaggag | tccaaggggt | 480 |
| aaaaacatac | aggggggaa | gaccctctcc | gtgtctcagc | tggagctcca | ggatagtggc | 540 |
| acctggacat | gcactgtctt | gcagaaccag | aagaaggtgg | agttcaaaat | agacatcgtg | 600 |
| gtgctagct | | | | | | 609 |

<210> SEQ ID NO 10
<211> LENGTH: 203
<212> TYPE: PRT
<213> ORGANISM: Artificial
<220> FEATURE:
<223> OTHER INFORMATION: Synthetic

<400> SEQUENCE: 10

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala
            195                 200

<210> SEQ ID NO 11
<211> LENGTH: 8
<212> TYPE: PRT
<213> ORGANISM: Artificial
<220> FEATURE:
<223> OTHER INFORMATION: Synthetic

<400> SEQUENCE: 11

Gly Asp Tyr Tyr Trp Ser Trp Ile
1               5

<210> SEQ ID NO 12
<211> LENGTH: 16
<212> TYPE: PRT
<213> ORGANISM: Artificial
<220> FEATURE:
<223> OTHER INFORMATION: Synthetic

<400> SEQUENCE: 12

Tyr Ile Ser Ser Ser Gly Asn Thr Tyr Tyr Asn Pro Ser Leu Thr Ser
1               5                   10                  15

<210> SEQ ID NO 13
<211> LENGTH: 19
<212> TYPE: PRT
<213> ORGANISM: Artificial
<220> FEATURE:
<223> OTHER INFORMATION: Synthetic

<400> SEQUENCE: 13

Ala Arg Glu Arg Val Leu Leu Trp Leu Gly Phe Pro Arg Gly Gly
1               5                   10                  15

Leu Asp Tyr

<210> SEQ ID NO 14
<211> LENGTH: 13
<212> TYPE: PRT
<213> ORGANISM: Artificial
<220> FEATURE:
<223> OTHER INFORMATION: Synthetic

<400> SEQUENCE: 14

Arg Ala Ser His Ser Val Ser Arg Ala Tyr Leu Ala Trp
1               5                   10

<210> SEQ ID NO 15
<211> LENGTH: 9
<212> TYPE: PRT
<213> ORGANISM: Artificial
<220> FEATURE:
<223> OTHER INFORMATION: Synthetic

<400> SEQUENCE: 15

Gly Thr Ser Ser Arg Ala Thr Gly Ile
1               5

<210> SEQ ID NO 16
<211> LENGTH: 11
<212> TYPE: PRT
<213> ORGANISM: Artificial
<220> FEATURE:

```
<223> OTHER INFORMATION: Synthetic

<400> SEQUENCE: 16

Gln Gln Tyr Gly Gly Ser Pro Trp Phe Gly Gln
1               5                   10
```